United States Patent [19]

Yamada et al.

[11] Patent Number: 4,874,760

[45] Date of Patent: Oct. 17, 1989

[54] 4,7-DIHYDROISOTHIAZOLO(5,4-B)PYRIDINE DERIVATIVES AND CARDIOVASCULAR TREATING AGENTS CONTAINING SAID DERIVATIVES

[75] Inventors: Shin-ichi Yamada, Fukushima; Takao Goto, Koori; Toshihisa Mashiko, Fukushima; Kentaro Kogi, Shiraishi; Yukiko Oguchi; Senichi Narita, both of Fukushima, all of Japan

[73] Assignee: Toa Eiyo, Ltd., Tokyo, Japan

[21] Appl. No.: 140,999

[22] Filed: Jan. 5, 1988

[30] Foreign Application Priority Data

Jan. 9, 1987 [JP] Japan .................. 62-1782

[51] Int. Cl.$^4$ ................ A61K 31/435; A61K 31/535; C07D 513/04
[52] U.S. Cl. ......................... 514/234.2; 514/253; 514/301; 544/127; 544/362; 546/114
[58] Field of Search ............... 544/127, 362; 546/114; 514/234.2, 253, 301

[56] References Cited

FOREIGN PATENT DOCUMENTS 62-298593  12/1987  Japan .

Primary Examiner—Robert W. Ramsuer
Attorney, Agent, or Firm—Sherman and Shalloway

[57] ABSTRACT

A 4,7-dihydroisothiazole[5,4-b]pyridine derivative represented by the general formula

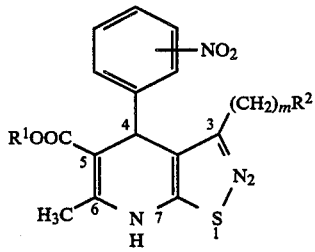

wherein
R$^1$ represents an alkyl group which may be substituted,
R$^2$ represents a hydrogen atom, a hydroxyl group, a benzyloxy group, a lower alkoxy group, a group of the formula

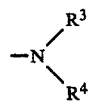

in which R$^3$ and R$^4$ are identical or different and each represents a hydrogen atom, a lower alkyl group, an aralkyl group, an aralkynyl group, an aryloxyalkyl group, an arylaminoalkyl group, a pyridylalkyl group or a benzazolylalkyl group, or R$^3$ and R$^4$ form a ring and represent a group of the formula

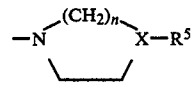

where X represents a methine group, a nitrogen atom or an oxygen atom, n is an integer of 1 or 2, and when X is a methine group or a nitrogen atom, R$^5$ represents a hydrogen atom, a lower alkyl group, a lower hydroxyalkyl group, an aryl group, an aryloxy group, an aralkyl group, a furoyl group, a pyridyl group or a diphenylmethane group each of which group may be substituted, and
m is an integer of 1 to 3,
or an acid addition salt thereof. Processes for producing said derivative and a cardiovascular treating agent comprising said derivative as an active ingredient are also provided.

4 Claims, No Drawings

4,7-DIHYDROISOTHIAZOLO(5,4-B)PYRIDINE DERIVATIVES AND CARDIOVASCULAR TREATING AGENTS CONTAINING SAID DERIVATIVES

This invention relates to novel 4,7-dihydroisothiazolo[5,4-b]pyridine derivatives, processes for production thereof, and to cardiovascular treating agents comprising said derivatives as active ingredients.

It is known that compounds having a calcium antagonizing action are used for the treatment of cardiovascular diseases such as angina pectoris, hypertension and cerebral blood flow disorder. Particularly, a series of 1,4-dihydropyridine derivatives have attracted attention as calcium antagonists. Nifedipine (see U.S. Pat. No. 3,485,847) and nicardipine (see Japanese Laid-Open Patent Publication No. 109384/1974), for example, may be cited as calcium antagonists having practical values.

We have worked extensively for a novel compound useful as an agent for treating cardiovascular diseases and now found that novel 4,7-dihydroisothiazolo[5,4-b]pyridine derivatives have strong calcium antagonizing activity and strong antihypertensive activity based on it, coronary blood flow increasing activity, and total peripheral resistance, and show an excellent efficacy as a cardiovascular treating agent.

Thus, the present invention provides a 4,7-dihydroisothiazolo[5,4-b]pyridine derivative represented by the general formula

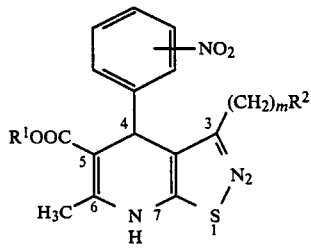

I wherein $R^1$ represents an alkyl group which may be substituted, $R^2$ represents a hydrogen atom, a hydroxyl group, a benzyloxy group, a lower alkoxy group, a group of the formula

in which $R^3$ and $R^4$ are identical or different and each represents a hydrogen atom, a lower alkyl group, an aralkyl group, an aralkynyl group, an aryloxyalkyl group, an arylaminoalkyl group, a pyridylalkyl group or a benzazolylalkyl group, or $R^3$ and $R^4$ form a ring and represent a group of the formula

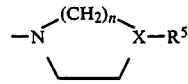

where X represents a methine group, a nitrogen atom or an oxygen atom, n is an integer of 1 or 2, and when X is a methine group or a nitrogen atom, $R^5$ represents a hydrogen atom, a lower alkyl group, a lower hydroxyalkyl group, an aryl group, an aryloxy group, an aralkyl group, a furoyl group, a pyridyl group or a diphenylmethane group each of which group may be substituted, and m is an integer of 1 to 3, or an acid addition salt thereof.

Linear or branched alkyl groups having 1 to 8 carbon atoms may be cited as examples of the alkyl group for $R^1$ in the compound of formula I. The alkyl group may be substituted by an alkoxy, amino, alkylamino or aralkylamino group. The lower alkoxy group for $R^2$ may be for example linear or branched alkoxy groups having 1 to 5 carbon atoms. The lower alkyl group for $R^3$ and $R^4$ may be for example linear or branched alkyl groups having 1 to 5 carbon atoms. The aromatic ring or pyridyl ring in the aralkyl, aralkynyl, aryloxyalkyl, arylaminoalkyl, pyridylalkyl or benzazolylalkyl group for $R^3$ and $R^4$ may be substituted by a hydroxyl group or a lower alkoxy group. Examples of the lower alkyl group for $R^5$ are linear or branched alkyl groups having 1 to 5 carbon atoms. The lower hydroxyalkyl group for $R^5$ may be for example linear or branched hydroxyalkyl groups having 1 to 5 carbon atoms. The aromatic ring, furoyl ring or pyridyl ring in the aryl, aryloxy, aralkyl, furoyl, pyridyl or diphenylmethane group for $R^5$ may be substituted by a lower alkyl group, a lower alkoxy group, a halogen atom, a nitro group, an amino group, a trifluoromethyl group or a cyano group. X represents a methine group, a nitrogen atom or an oxygen atom. m represents an integer of 1 to 3, and n represents an integer of 1 or 2.

The 4,7-dihydroisothiazolo[5,4-b]pyridine derivatives (I) of this invention are novel compounds not described in the literature, and have antihypertensive activity, coronary blood flow increasing activity and total peripheral resistance based on their strong calcium antagonizing activity. Hence, they are useful for treating cardiovascular diseases.

The following compounds Nos. 1 to 70 may be cited as examples of the compounds of formula I.

1 ethyl 3-benzyloxymethyl-6-methyl-4-(3-nitrophenyl)-4,7-dihydroisothiazolo[5,4-b]pyridine-5-carboxylate 2 ethyl 3-(2-benzyloxyethyl)-6-methyl-4-(3-nitrophenyl)-4,7-dihydroisothiazolo[5,4-b]pyridine-5-carboxylate 3 ethyl 3-(3-benzyloxypropyl)-6-methyl-4-(3-nitrophenyl)-4,7-dihydroisothiazolo[5,4-b]pyridine-5-carboxylate 4 ethyl 3-hydroxymethyl-6-methyl-4-(3-nitrophenyl)-4,7-dihydroisothiazolo[5,4-b]pyridine-5-carboxylate 5 ethyl 3-(2-hydroxyethyl)-6-methyl-4-(3-nitrophenyl)-4,7-dihydroisothiazolo[5,4-b]pyridine-5-carboxylate 6 ethyl 3-(3-hydroxypropyl)-6-methyl-4-(3-nitrophenyl)-4,7-dihydroisothiazolo[5,4-b]pyridine-5-carboxylate 7 ethyl 3-dimethylaminomethyl-6-methyl-4-(3-nitrophenyl)-4,7-dihydroisothiazolo[5,4-b]pyridine-5-carboxylate 8 ethyl 3-[N-(2-(3,4-dimethoxyphenyl)ethyl)-N-methylaminomethyl]-6-methyl-4-(3-nitrophenyl)-4,7-dihydroisothiazolo[5,4-b]pyridine-5-carboxylate 9 ethyl 3-[N-(3-(3-methoxyphenoxy)propyl)-N-methylaminomethyl]-6-methyl-4-(3-nitrophenyl)-4,7-dihydroisothiazolo[5,4-b]pyridine-5-carboxylate 10 ethyl 3-[N-(2-(2-pyridyl)ethyl)-N-methylaminomethyl]-6-methyl-4-(3-nitrophenyl)-4,7-dihydroisothiazolo[5,4-b]pyridine-5-carboxylate
11 2-(N-benzyl-N-methylamino)ethyl 2,6-dimethyl-4-(3-nitrophenyl)-4,7-dihydroisothiazolo[5,4-b]pyridine-5-carboxylate
12 2-(N-benzyl-N-methylamino)ethyl 3-[N-(2-(3,4-dimethoxyphenyl)ethyl)-N-methylaminomethyl]-6-methyl-4-(3-nitrophenyl)-4,7-dihydroisothiazolo[5,4-b]pyridine-5-carboxylate
13 2-(N-benzyl-N-methylamino)ethyl 3-[4-(4-fluorophenyl)-1-piperazinylmethyl]-6-methyl-4-(3-nitrophenyl)-4,7-dihydroisothiazolo[5,4-b]pyridine-5-carboxylate
14 2-(N-benzyl-N-methylamino)ethyl 3-[4-(4,4'-difluorobenzhydryl)-1-piperazinylmethyl]-6-methyl-4-(3-nitrophenyl)-4,7-dihydroisothiazolo[5,4-b]pyridyl-5-carboxylate
15 ethyl 3-(2-dimethylaminoethyl)-6-methyl-4-(3-nitrophenyl)-4,7-dihydroisothiazolo-[5,4-b]pyridine-5-carboxylate
16 ethyl 3-[2-(N-benzyl-N-methylamino)ethyl]-6-methyl-4-(3-nitrophenyl)-4,7-dihydroisothiazolo[5,4-b]pyridine-5-carboxylate
17 ethyl 3-[2-(N-(2-(3,4-dimethoxyphenyl)ethtyl)-N-methylamino)ethyl]-6-methyl-4-(3-nitrophenyl)-4,7-dihydroisothiazolo[5,4-b]pyridine-5-carboxylate
18 ethyl 3-[2-(N-(3-(3-methoxyphenoxy)propyl)-N-methylamino)ethyl]-6-methyl-4-(3-nitrophenyl)-4,7-dihydroisothiazolo[5,4-b]pyridine-5-carboxylate
19 ethyl 3-[2-(N-methylpropargylamino)ethyl]-6-methyl-4-(3-nitrophenyl)-4,7-dihydroisothiazolo-[5,4-b]pyridine-5-carboxylate
20 ethyl 3-[2-(1-piperazinyl)ethyl]-6-methyl-4-(3-nitrophenyl)-4,7-dihydroisothiazolo[5,4-b]pyridine-5-caboxylate
21 ethyl 3-[2-(4-phenyl-1-piperazinyl)ethyl]-6-methyl-4-(3-nitrophenyl)-4,7-dihydroisodithiazolo[5,4-b]pyridine-5-carboxylate
22 ethyl 3-[2-(4-(4-chlorophenyl)-1-piperazinyl)ethyl]-6-methyl-4-(3-nitrophenyl)-4,7-dihydroisothiazolo[5,4-b]pyridine-5-carboxylate
23 ethyl 3-[2-(4-(4-fluorophenyl)-1-piperazinyl)ethyl]-6-methyl-4-(3-nitrophenyl)-4,7-dihyhdroisothiazolo[5,4-b]pyridine-5-carboxylate
24 ethyl 3-[2-(4-(3,4-dimethylphenyl)-1-piperazinyl)ethyl]-6-methyl-4-(3-nitrophenyl)-4,7-dihydroisothiazolo[5,4-b]pyridine-5-carboxylate
25 ethyl 3-[2-(4-(2,3-dimethylphenyl)-1-piperazinyl)ethyl]-6-methyl-4-(3-nitrophenyl)-4,7-dihydroisothiazolo[5,4-b]pyridine-5-carboxylate
26 ethyl 3-[2-(4-(2-methoxyphenyl)-1-piperazinyl)ethyl]-6-methyl-4-(3-nitrophenyl)-4,7-dihydroisothiazolo[ 5,4-b]pyridine-5-carboxylate
27 ethyl 3-[2-(4-(4-methoxyphenyl)-1-piperazinyl)ethyl]-6-methyl-4-(3-nitrophenyl)-4,7-dihydroisothiazolo[5,4-b]pyridine-5-carboxylate
28 ethyl 3-[2-(4-(2-ethoxyphenyl)-1-piperazinyl)ethyl]-6-methyl-4-(3-nitrophenyl)-4,7-dihydroisothiazolo[5,4-b]pyridine-5-carboxylate
29 ethyl 3-[2-(4-(3,4-dimethoxyphenyl)-1-piperazinyl)ethyl]-6-methyl-4-(3-nitrophenyl)-4,7-dihydroisothiazolo[5,4-b]pyridine-5-carboxylate
30 ethyl 3-[2-(4-(4-trifluoromethylphenyl)-1-piperazinyl)ethyl]-6-methyl-4-(3-nitrophenyl)-4,7-dihydroisothiazolo[5,4-b]pyridine-5-carboxylate
31 ethyl 3-[2-(4-(4-cyanophenyl)-1-piperazinyl)ethyl]-6-methyl-4-(3-nitrophenyl)-4,7-dihydroisothiazolo[5,4-b]pyridine-5-carboxylate
32 ethyl 3-[2-(4-(4-aminophenyl)-1-piperazinyl)ethyl]-6-methyl-4-(3-nitrophenyl)-4,7-dihydroisothiazolo[5,4-b]pyridine-5-carboxylate
33 ethyl 3-[2-(4-(4-nitrophenyl)-1-piperazinyl)ethyl]-6-methyl-4-(3-nitrophenyl)-4,7-dihydroisothiazolo[5,4-b]pyridine-5-carboxylate
34 ethyl 3-[2-(4-(2-pyridyl)-1-piperazinyl)ethyl]-6-methyl-4-(3-nitrophenyl)-4,7-dihydroisothiazolo[5,4-b]pyridine-5-carboxylate
35 ethyl 3-[2-(4-methyl-1-piperazinyl)ethyl]-6-methyl-4-(3-nitrophenyl)-4,7-dihydroisothiazolo[5,4-b]pyridine-5-carboxylate
36 ethyl 3-[2-(4-(2-hydroxy)ethyl)-1-piperazinyl)ethyl]-6-methyl-4-(3-nitrophenyl)-4,7-dihydroisothiazolo[5,4-b]pyridine-5-carboxylate
37 ethyl 3-[2-(4-cyclohexyl-1-piperazinyl)ethyl]-6-methyl-4-(3-nitrophenyl)-4,7-dihydroisothiazolo[ 5,4-b]pyridine-5-carboxylate
38 ethyl 3-[2-(4-benzyl-1-piperazinyl)ethyl]-6-methyl-4-(3-nitrophenyl)-4,7-dihydroisothiazolo[5,4-b]pyridine-5-carboxylate
39 ethyl 3-[2-(4-(2-fluoroyl)-1-piperazinyl)ethyl]-6-methyl-4-(3-nitrophenyl)-4,7-dihydroisothiazolo[5,4-b]pyridine-5-carboxylate
40 ethyl 3-[2-(4-(4,4'-difluorobenzhydryl)-1-piperazinyl)ethyl]-6-methyl-4-(3-nitrophenyl)-4,7-dihydroisothiazolo[5,4-b]pyridine-5-carboxylate
41 2-(N-benzyl-N-methylamino)ethyl 3-[2-(4-(4-fluorophenyl)-1-piperazinyl)ethyl]-6-methyl-4-(3-nitrophenyl)-4,7-dihydroisothiazolo[5,4-b]pyridine-5-carboxylate
42 methyl 3-[2-(4-phenyl-1-piperazinyl)ethyl]-6-methyl-4-(2-nitrophenyl)-4,7-dihydroisothiazolo[5,4-b]pyridine-5-carboxylate
43 methyl 3-[2-(4-(4-fluorophenyl)-1-piperazinyl)ethyl]-6-methyl-4-(2-nitrophenyl)-4,7-dihydroisothiazolo[5,4-b]pyridine-5-carboxylate
44 ethyl 3-[2(1-pyrrolidinyl)ethyl]-6-methyl-4-(3-nitrophenyl)-4,7-dihydroisothiazolo[5,4-b]pyridine-5-carboxylate
45 ethyl 3-(2-piperidinoethyl)-6-methyl-4-(3-nitrophenyl)-4,7-dihydroisothiazolo[5,4-b]pyridine-5-carboxylate
46 ethyl 3-(2-morpholinoethyl)-6-methyl-4-(3-nitrophenyl)-4,7-dihydroisothiazolo[5,4-b]pyridine-5-carboxylate
47 ethyl 3-[2-(4-phenyl-1-piperidinyl)ethyl]-6-methyl-4-(3-nitrophenyl)-4,7-dihydroisothiazolo[5,4-b]pyridine-5-carboxylate
48 ethyl 3-[2-(4-(3-methoxyphenoxy)-1-piperizinyl)ethyl]-6-methyl-4-(3-nitrophenyl)-4,7-dihydroisothiazolo[5,4-b]pyridine-5-carboxylate
49 ethyl 3-[2-(2-(4-phenylamino)ethylamino)ethyl]-6-methyl-4-(3-nitrophenyl)-4,7-dihydroisothiazolo[5,4-b]pyridine-5-carboxylate
50 ethyl 3-[2-(2-hydroxy-3-phenoxypropylamino)ethyl]-6-methyl-4-(3-nitrophenyl)-4,7-dihydroisothiazolo[5,4-b]pyridine-5-carboxylate
51 ethyl 3-[2-(N-(2-(2-benzothiazolyl)ethyl)-N-methylamino)ethyl]-6-methyl-4-(3-nitrophenyl)-4,7-dihydroisothiazolo[5,4-b]pyridine-5-carboxylate
52 ethyl 3-[3-(N-(2-(3,4-dimethoxyphenyl)ethyl)-N-methylamino)propyl]-6-methyl-4-(3-nitrophenyl)-4,7-dihydroisothiazolo[5,4-b]pyridine-5-carboxylate 53 ethyl 3-[3-(N-(3-(3-methoxyphenoxy)propyl)-N-methylamino)propyl]-6-methyl-4-(3-nitrophenyl)-4,7-dihydroisothiazolo[5,4-b]pyridine-5-carboxylate 54 ethyl 3-[3-(N-methylpropargylamino)propyl]-6-methyl-4-(3-nitrophenyl)-4,7-dihydroisothiazolo[5,4-b]pyridine-5-carboxylate 55 ethyl 3-[3-(4-fluorophenyl-1-piperazinyl)propyl]-6-methyl-4-(3-nitrophenyl)-4,7-dihydroisothiazolo[5,4-b]pyridine-5-carboxylate 56 ethyl 3-[3-(4-(4,4'-difluorobenzhydryl)-1-piperazinyl)propyl]-6-methyl-4-(3-nitrophenyl)-4,7-dihydroisothiazolo[5,4-b]pyridine-5-carboxylate 57 (+)-5-[(S)-2-methoxy-2-phenylethyl]3,6-dimethyl-4-(3-nitrophenyl)-4,7-dihydroisothiazolo[5,4-b]pyridine-5-carboxylate 58 (−)-5-[(S)-2-methoxy-2-phenylethyl]3,6-dimethyl-4-(3-nitrophenyl)-4,7-dihydroisothiazolo[5,4-b]pyridine-5-carboxylate 59 (+)-ethyl 3-[(R)-N-methyl-alpha-methylphenylethylaminomethyl]-6-methyl-4-(3-nitrophenyl)-4,7-dihydroisothiazolo[5,4-b]pyridine-5-carboxylate 60 (−)-ethyl 3-[(R)-N-methyl-alpha-methylphenylethylaminomethyl]-6-methyl-4-(3-nitrophenyl)-4,7-dihydroisothiazolo[5,4-b]pyridine-5-carboxylate 61 (+)-ethyl 3-[(S)-N-methyl-alpha-methylphenylethylaminomethyl]-6-methyl-4-(3-nitrophenyl)-4,7-dihydroisothiazolo[5,4-b]pyridine-5-carboxylate 62 (−)-ethyl 3-[(S)-N-methyl-alpha-methylphenylethylaminomethyl]-6-methyl-4-(3-nitrophenyl)-4,7-dihydroisothiazolo[5,4-b]pyridine-5-carboxylate 63 (+)-ethyl 3-[2-((S)-alpha-methoxybenzylcarbonyloxy)ethyl]-6-methyl-4-(3-nitrophenyl)-4,7-dihydroisothiazolo[5,4-b]pyridine-5-carboxylate 64 (−)-ethyl 3-[2-((S)-alpha-methoxybenzylcarbonyloxy)ethyl]-6-methyl-4-(3-nitrophenyl)-4,7-dihydroisothiazolo[5,4-b]pyridine-5-carboxylate 65 (−)-ethyl 3-[2-((R)-alpha-methoxybenzylcarbonyloxy)ethyl]-6-methyl-4-(3-nitrophenyl)-4,7-dihydroisothiazolo[5,4-b]pyridine-5-carboxylate 66 (+)-ethyl 3-[2-((R)-alpha-methoxybenzylcarbonyloxy)ethyl]-6-methyl-4-(3-nitrophenyl)-4,7-dihydroisothiazolo[5,4-b]pyridine-5-carboxylate 67 (+)-ethyl 3-(2-hydroxyethyl)-6-methyl-4-(3-nitrophenyl)-4,7-dihydroisothiazolo[5,4-b]pyridine-5-carboxylate 68 (−)-ethyl 3-(2-hydroxyethyl)-6-methyl-4-(3-nitrophenyl)-4,7-dihydroisothiazolo[5,4-b]pyridine-5-carboxylate 69 (+)-ethyl 3-[2-(4-phenyl-1-piperazinyl)ethyl]-6-methyl-4-(3-nitrophenyl)-4,7-dihydroisothiazolo[5,4-b]pyridine-5-carboxylate 70 (−)-ethyl 3-[2-(4-phenyl-1-piperazinyl)ethyl]-6-methyl-4-(3-nitrophenyl)-4,7-dihydroisothiazolo[5,4-b]pyridine-5-carboxylate The compound of formula I may be produced by the following processes.

For example, a compound of the following general formula

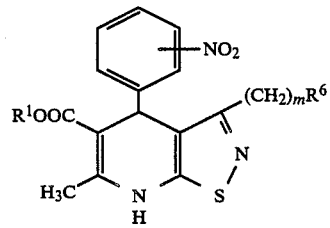

Ia wherein $R^1$ and m are as defined hereinabove, and $R^6$ represents a hydroxyl group, a benzyloxy group or a lower alkoxy group, can be produced by reacting a 5-aminoisothiazole derivative of the following general formula

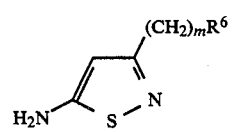

II wherein $R^6$ and m are as defined above, with an α,β-unsaturated ketone derivative of the following formula

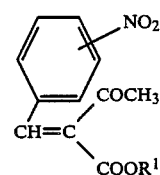

III wherein $R^1$ is as defined above.

This reaction may be carried out without a solvent, but preferably in the presence of a solvent. The solvent may be an inert solvent. Examples include alcohols such as methanol, ethanol, isopropanol and tert-butanol, ethers such as 1,2-dimethoxyethane and tetrahydrofuran, aromatic hydrocarbons such as benzene, toluene and xylene, amides such as dimethylacetamide and dimethylformamide and sulfoxides such as dimethyl sulfoxide and sulfolane.

The reaction temperature is from room temperature to the boiling point of the solvent, preferably 60° to 100° C. Preferably, the reaction is carried out in an atmosphere of an inert gas such as nitrogen or argon. The reaction usually comes to completion in several hours to several days.

As an alternative process, a compound of the general formula

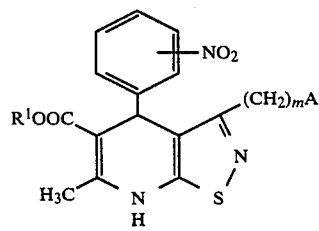

Ic wherein $R^1$ and m are as defined above,
A represents the group

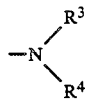

or the group

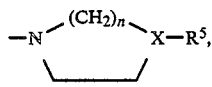

and X, $R^3$, $R^4$, $R^5$ and n are as defined above, can be obtained by reacting a compound of the general formula Ib

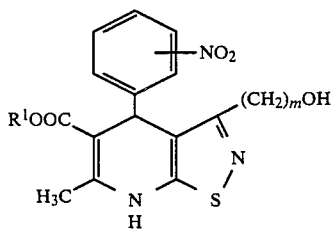

wherein $R^1$ and m are as defined above, with methanesulfonyl chloride, p-toluenesulfonyl chloride or a halogenating agent to convert it into a mesylate compound, tosylate compound or a halogen compound, and reacting the product with a compound of the general formula

IV

wherein $R^3$ and $R^4$ are as defined, or a compound of the general formula

V

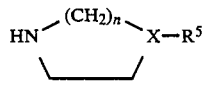

wherein X, $R^5$ and n are as defined above.

Since the compound of formula I has an asymmetric carbon atom at the 4-position, it can be separated into optical isomers based on the asymmetric carbon. For example, the use of an optically active compound as the compound of formula Ib gives an optically active compound of formula I. The optically active compound of formula Ib can be produced, for example, by treating a 4-position diastereoisomer ester mixture of the general formula

VI

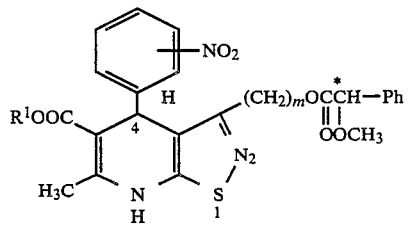

wherein $R^1$ and m are as defined above, by silica gel column chromatography, recrystallization and high-performance liquid chromatography in suitable combinations to separate it into the individual diastereoisomers, and hydrolyzing the ester groups to give optically active alcohol derivatives of the following formulae Id

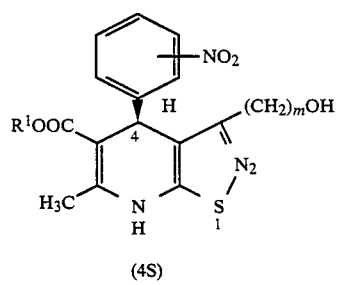

(4S)

and

Ie

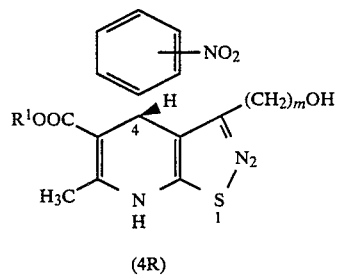

(4R)

wherein $R^1$ and m are as defined above.

These optically active alcohol derivatives can be converted to compounds of formula I by the process described hereinabove.

Examples of the compounds IV and V used in the above reactions include methylamine, dimethylamine, ethylamine, diethylamine, N-methyl-N-benzylamine, R-(+)-N-methyl-alpha-methylbenzylamine, S-(—)-N-methyl-alpha-methylbenzylamine, N-methylhomoveratrylamine, N-methyl-N-3-(3-methoxyphenoxy)propylamine, N-methyl-N-2-(2-pyridyl)ethylamine, 1-phenylpiperazine, 1-(2-methoxyphenyl)piperazine, 1-(4-fluorophenyl)piperazine, 1-(4,4'--difluorobenzhydryl)piperazine, N-methyl-N-propargylamine, 2-hydroxy-3-phenoxypropylamine, 3-N-methylamino-1-benzylpyrrolidine, and N-methyl-N-2-(2-benzothiazolyl)ethylamine.

The reaction of the compound of formula Ib with methanesulfonyl chloride or p-toluenesulfonyl chloride is carried out in a solvent in the presence of a base such as triethylamine or pyridine. The solvent may be, for example, tetrahydrofuran, diethyl ether, methylene chloride, chloroform, benzene and toluene. The reaction temperature is from −20° C. to the boiling point of the solvent, preferably from −20° C. to room temperature. This reaction is preferably carried out in an atmosphere of an inert gas such as nitrogen or argon. The reaction comes to completion in 1 to 24 hours.

The reaction of the compound of formula Ib with the halogenating agent is carried out in the absence or presence of a solvent. The halogenating agent may be for example thionyl chloride, phosphorus tribromide, phosphorus pentachloride and phosphorus oxychloride. Examples of the solvent are benzene, toluene, xylene, dimethyl ether, methylene chloride and chloroform. The reaction temperature is preferably 0° to 150° C. The reaction comes to completion in 1 to 24 hours.

The second-step reaction may be carried out in the absence of solvent, or in the presence of a solvent which is not involved in the reaction, such as ethanol, benzene, toluene and xylene. This reaction is preferably carried out in the presence of an excess of the amine (IV) or (V) or in the presence of triethylamine or pyridine. The reaction temperature is preferably 60° to 120° C. The reaction usually comes to completion in 1 to 8 hours.

The compound of formula Ib may also be produced by reacting a compound of formula Ia in which $R^6$ is a benzyloxy group or a lower alkoxy group, with trimethylsilyl iodide in a solvent, or with boron trifluoride etherate in the presence of methyl sulfide or ethanethiol. The solvent may be for example tetrahydrofuran, diethyl ether, methylene chloride and chloroform. The reaction tempeature is from −20° C. to the boiling point of the solvent. Usually, the reaction end in 30 minutes to 72 hours.

The product may be isolated and purified by treating it with conventional methods, for example extraction, column chromatography and recrystallization in suitable combinations.

If desired, the compound of formula I may be converted to its acid addition salt. Examples of suitable acids for making the acid addition salts are physiologically acceptable acids such as hydrochloric acid, sulfuric acid, fumaric acid, maleic acid and oxalic acid.

The 5-aminoisothiazole derivative (II) used in this invention is a novel compound, and can be obtained in good yields by subjecting a thioamide compound represented by the general formula

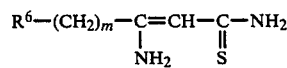    VII wherein $R^6$ and m are as defined above, to intramolecular cyclization reaction.

The thioamide compound (VII) may be produced, for example, from an ester represented by the following general formula in three steps.

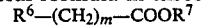    VIII wherein $R^6$ and m are as defined above, and
$R^7$ represents a lower alkyl group.

α,β-unsaturated ketone derivatives of formula III, some of which are novel compounds, can be easily produced by condensation reaction between nitrobenzaldehyde and an acetoacetic ester represented by the general formula

    IX wherein $R^1$ is as defined above.

The compounds of formula I in accordance with this invention may be administered orally or parenterally for therapeutic purposes.

For oral administration, the compounds I may be in the form of solid formulations such as powders, granules, capsules and tablets, or liquid formulations such as syrups and elixirs. For parenteral administrations, the compounds may be in the form of an injecting preparation, a suppository or an external skin applying agent. These formulations may be produced by conventional methods using pharmaceutically acceptable additives. They may be prepared into long acting formulations by known techniques.

For example, a powder may be prepared by mixing the active ingredient and a vehicle such as lactose, starch, crystalline cellulose, calcium lactate, magnesium metasilicate aluminate and silicic anhydride. Granules may be prepared, for example, by adding sugar, a binder such as hydroxypropyl cellulose and polyvinylpyrrolidone and a disintegrants such as carboxymethyl cellulose and carboxymethyl cellulose calcium to the aforesaid powder, and granulating the mixture in the wet or dry state. Tablets may be prepared by tableting the aforesaid powder or granules either singly or in combination with a lusterant such as magnesium stearate and talc. Enteric-coated formulations may be prepared by coating the granules or the tablets with an enteric base such as hydroxypropyl methyl cellulose phthalate, methacrylic acid or a methyl methacrylate copolymer. Long acting formulations may be prepared by coating the above granules or tablets with a hardened oil. Hard capsules may be formulated by filling the powder or granules into capsules. Soft capsules may be formulated by dissolving the active ingredient in glycerol, polyethylene glycol, sesame oil or olive oil and coating the solution with a gelatin film.

As liquid formulations, a clear syrup, for example, may be prepared by dissolving the active ingredient and a sweetening agent such as sugar, sorbitol or glycerol in water. An elixir may be prepared by adding an essential oil or ethanol. An emulsion or suspension may be prepared by adding gum arabic, tragacanth, polysorbate 80 or carboxymethyl cellulose sodium to the resulting syrup. If desired, a corigent, a coloring agent and a preservative may be added to these liquid formulations.

An injectable preparation may be formed by dissolving the active ingredient, optionally with a pH adjusting agent such as hydrochloric acid, sodium hydroxide, an emulsifier, sodium lactate, sodium mono-hydrogen phosphate or sodium dihydrogen phosphate, or an isotonic agent such as sodium chloride or glucose, in injectable distilled water, aseptically filtering the solution, and filling the filtered solution into ampoules. By adding mannitol, dextrin, cyclodextrin or gelatin to the above solution, and lyophilizing the solution under vacuum, an injectable preparation to be dissolved prior to use may be produced. An injectable emulsion may be prepared by adding lecithin, polysorbate 80, polyoxyethylene hardened castor oil to the active ingredient, and emulsifying the mixture in water.

A suppository may be prepared by moistening and molding a mixture of the active ingredient and a base for a suppository such as cacao butter, a tri-, di- or monoglyceride of a fatty acid, or polyethylene glycol, pouring the molten mixture into a mold, and then cooling it, or by dissolving the active ingredient in polyethylene glycol or soybean oil, and coating the solution with a gelatin film.

An agent for external application to the skin may be, or example, an ointment which is obtained by adding the active ingredient to white vaseline, beeswax, liquid paraffin or polyethylene glycol, and kneading the mixture optionally at an elevated temperature, or a tape agent which is prepared by kneading the active ingredient with an adhesive such as rosin or an alkyl acrylate polymer, and spreading the mixture on a non-woven fabric of polyethylene, or the like.

The dosage of the 4,7-dihydroisothiazolo[5,4-b]pyridine derivative of this invention varies depending upon the age, body weight and condition of the patient. Usually, it is about 0.1 to 1,000 mg per day to be administered once a day, or several times a day dividedly.

The following Test Example, Referential Examples, Examples and Formulation Examples illustrate the present invention more specifically.

TEST EXAMPLE

The following compounds Ia to Ih which are within the formula I given hereinabove were subjected to a pharmacological test.

| Ia: | Compound No. 8 given hereinabove. |
|---|---|
| Ib: | Compound No. 9 given hereinabove. |
| Ic: | Compound No. 12 given hereinabove. |
| Id | Compound No. 13 given hereinabove. |
| Ie: | Compound No. 21 given hereinabove. |
| If: | Compound No. 23 given hereinabove. |
| Ig: | Compound No. 69 given hereinabove. |
| Ih: | Compound No. 70 given hereinabove. |

Test on calcium antagonizing activity

Female and male rabbits weighing 2 to 3 kg were used. They were anesthetized by intravenous injection of pentobarbital sodium, and sacrificed by bleeding from the femoral arteries. Immediately then, the artery was extracted from the chest, and a helical blood vessel specimen was prepared. The extracted vessel specimen was suspended under a tension of 1.5 g in a Magnus tube containing 10 ml of a nutrient solution (NaCl 147.2, KCl 5.4, $CaCl_2$ 2.2, $MgCl_2$ 1.0, $NaHCO_3$ 14.9 and glucose 5.6 mM) through which a gaseous mixture composed of 95% of oxygen and 5% of carbon dioxide was passed and which was kept at 37° C. As a control, 10-20 mM (of KCl was cumulatively administered (0.1 ml of 1M KCl solution each time) to cause vascular constriction stepwise, and a dose-response curve was obtained. Then, each of the test compounds was administered (in three doses), and 10 minutes later, a dose-response curve of KCl was again obtained. By taking the contraction height obtained by administering 40 mM of KCl as 100%, and the concentration of the test drug which inhibit the contraction height of the control to an extent of 50% was determined as an $ED_{50}$ value. The results are shown in Table 1.

TABLE 1

| Compound | $ED_{50}$ (M) |
|---|---|
| Ia | $6.0 \times 10^{-8}$ |
| Ib | $6.2 \times 10^{-8}$ |
| Ic | $2.25 \times 10^{-7}$ |
| Id | $>3 \times 10^{-7}$ |
| Ie | $3.3 \times 10^{-8}$ |
| If | $6.38 \times 10^{-8}$ |
| Ig | $>3 \times 10^{-7}$ |
| Ih | $2.5 \times 10^{-8}$ |

TABLE 1-continued

| Compound | $ED_{50}$ (M) |
|---|---|
| Nifedipine | $1.96 \times 10^{-8}$ |

Antihypertensive activity test

Male spontaneously hypertensive rats having a body weight of 280 to 350 g (systolic blood pressure 180-230 mmHg) were caused to abstain from food for about 15 hours, and then each of the test compounds was orally administered. Variations in systolic blood pressure were periodically measured by a programmed electrosphygmomanometer-type blood pressure measuring device (NARCO, PE-300). The results are shown in Table 2. In the table, the systolic blood pressures given in Table 2 show the maximum variations in each of the doses of the test compounds.

TABLE 2

| Compound | Dosage (mg/kg) | Systolic blood pressure (mmHg) |
|---|---|---|
| Ia | 1 | −6 |
|  | 3 | −26 |
|  | 10 | −82 |
|  | 30 | −119 |
| Ib | 3 | −30 |
|  | 10 | −76 |
|  | 30 | −108 |
| Ic | 3 | −37 |
|  | 10 | −92 |
|  | 30 | −135 |
| Id | 1 | −30 |
|  | 3 | −65 |
|  | 10 | −132 |
|  | 30 | −142 |
| Ie | 1 | −41 |
|  | 3 | −51 |
|  | 10 | −101 |
| If | 1 | −47 |
|  | 3 | −54 |
|  | 10 | −102 |
| Ih | 1 | −36 |
|  | 3 | −93 |
|  | 10 | −137 |
| Nifedipine | 1 | −29 |
|  | 3 | −42 |
|  | 10 | −71 |

The above results of Test Example demonstrate that the compounds of formula I provided by this invention have calcium antagonizing activity and antihypertensive activity based on it.

REFERENTIAL EXAMPLE 1

Production of 4-benzyloxy-3-ketobutanenitrile

In a stream of argon, 156.2 ml (0.248 mole) of a solution of 1.6 moles of n-butyllithiumhexane was added to 150 ml of anhydrous tetrahydrofuran. The mixture was cooled to −78° C., and a solution of 15.8 ml (0.293 mole) of acetonitrile in 50 ml of anhydrous tetrahydrofuran was added dropwise. The mixture was stirred at −78° C. for 1 hour. A solution of 55.2 g (0.248 mole) of ethylbenzyloxyacetate in 100 ml of anhydrous tetrahydrofuran was added dropwise. The mixture was stirred at −78° C. for 15 minutes and at room temperature for 50 minutes. The mixture was then poured into 200 ml of ice water. The aqueous layer was washed with ether, acidified with concentrated hydrochloric acid, and extracted with ether. The ether layer was washed with water and a saturated aqueous solution of sodium chloride, and dried over anhydrous magnesium sulfate. The solvent was evaporated under reduced pressure to give 70.9 g of crude 4-benzyloxy-3-ketobutanenitrile.

IR spectrum (neat cm$^{-1}$): 2250, 1735.

NMR spectrum (CDCl$_3$): δppm 3.59 (2H, s, CH$_2$CN) 4.07 (2H, s, CH$_2$) 4.53 (2H, s, CH$_2$) 7.31 (5H, s, benzene ring H)

In the same way, 5-benzyloxy-3-ketopentanenitrile was obtained (yield 80.3%).

IR spectrum (neat cm$^{-1}$): 2250, 1730

NMR spectrum (CDCl$_3$): δppm 2.77 (2H, t, J=6.0 Hz, CH$_2$) 3.48 (2H, s, CH$_2$) 3.71 (2H, t, J=6.0 Hz, CH$_2$) 4.48 (2H, s, CH$_2$) 7.28 (5H, s, benzene ring H)

REFERENTIAL EXAMPLE 2

Production of 6-benzyloxy-3-ketohexanenitrile

In a stream of argon, 248 ml of tetrahydrofuran was added to 26 g (0.65 mole) of 60% sodium hydride, and a solution of 72.2 g (0.325 moles) of ethyl 4-benzyloxybutyrate and 26.7 g (0.65 mole) of acetonitrile in 94 ml of anhydrous tetrahydrofuran was added dropwise over the course of 40 minutes, and the mixture was heated under reflux for 2.5 hours. After cooling, the reaction mixture was poured into ice water, and washed with a 1:1 mixture of hexane and ether. The aqueous layer was acidified with concentrated hydrochloric acid, and extracted with ether. The ether layer was washed with water and a saturated aqueous solution of sodium chloride, and then dried over anhydrous magnesium sulfate. The solvent was evaporated under reduced pressure. The resulting crude 6-benzyloxy-3-ketohexanenitrile was subjected to silica gel column chromatography. The column was eluted with a 1:1 mixture of hexane and ether to give 57.8 g (81.2%) of a pale yellow oily product.

IR spectrum (neat cm$^{-1}$): 2250, 1730

NMR spectrum (CDCl$_3$): δppm 1.82 (2H, quin, J=7.0 Hz, CH$_2$) 1.60 (2H, t, J=7.0 Hz, CH$_2$) 3.35 (2H, s, CH$_2$) 3.42 (2H, t, J=7.0 Hz, CH$_2$) 4.40 (2H, s, OCH$_2$) 7.24 (5H, s, benzene ring H)

REFERENTIAL EXAMPLE 3

Production of 3-amino-4-benzyloxy-2-butenenitrile

Ethanol (300 ml) was added to 70 g of the crude 4-benzyloxy-3-ketobutanenitrile obtained in Referential Example 1 and 20.1 g of ammonium nitrate. Ammonia was introduced for 30 minutes at room temperature, and then while the mixture was heated at 60° to 70° C., ammonia was introduced for 2 hours. After cooling, ethanol was evaporated under reduced pressure. The residue was extracted with chloroform, and the chloroform layer was washed with water and a saturated aqueous solution of sodium chloride, and then dried over anhydrous magnesium sulfate. The solvent was evaporated under reduced pressure. The resulting crude 3-amino-4-benzyloxy-2-butenenitrile was subjected to silica gel column chromatography, and the column was eluted with a 10:1 mixture of hexane and ethyl acetate to give 19.3 g of (yield from ethyl benzyloxy acetate, 37%).

IR spectrum (neat cm$^{-1}$): 3480, 3360, 3250, 2190, 1625

NMR spectrum (CDCl$_3$): δppm 3.85–4.60 (5H, m, CH$_2$×2, CH) 4.70–5.40 (2H, m, NH$_2$) 7.30 (5H, s, benzene ring H)

In the same way, 3-amino-5-benzyloxy-2-penteneni-trile was obtained (yield 64.7%).

IR spectrum (neat cm$^{-1}$): 3450, 3350, 3250, 2200

NMR spectrum (CDCl$_3$): δppm 2.40 (2H, t, J=6.0 Hz, CH$_2$) 2.72 (2H, q, J=6.0 Hz, CH$_2$) 3.47–4.10 (3H, m, CH$_2$, CH) 4.60 (2H, s, CH$_2$) 4.81–5.44 (2H, br, NH$_2$, disappeared by D$_2$O) 7.30 (5H, s, benzene ring H)

In the same way, 3-amino-6-benzyloxyhexene-nitrile (yield 85.6%) was obtained.

IR spectrum (neat cm$^{-1}$): 3450, 3350, 3250, 2180, 1630

NMR spectrum (CDCl$_3$): δppm 1.50–2.65 (4H, m, CH$_2$×2) 3.49, 3.52 (2H, t, J=7.0 Hz, CH$_2$) 3.75, 4.00 (1H, s, CH) 4.49 (2H, s, OCH$_2$) 4.52–5.30 (2H, m, NH$_2$) 7.30 (5H, m, benzene ring H)

REFERENTIAL EXAMPLE 4

Production of 3-amino-4-benzyloxy-2-butenethioamide

Pyridine (28 ml) was added to 19.7 g (0.106 mole) of 5-amino-4-benzyloxy-2-butenenitrile obtained in Referential Example 3, and then while the mixture was heated at 40° to 45° C., hydrogen sulfide was introduced for 5 hours. After cooling, pyridine was evaporated under reduced pressure. When methylene chloride and hexane were added to the residue 10.3 g (43.8%) of 3-amino-4-benzyloxy-2-butenethioamide was obtained as brown scaly crystals having a melting point of 155° to 158° C.

IR spectrum (KBr cm$^{-1}$): 3450, 3340, 3280, 1620, 1600

NMR spectrum (CDCl$_3$+(CD$_3$)$_2$SO) δppm 4.02 (2H, s, CH$_2$) 4.51 (2H, s, CH$_2$) 7.32 (5H, s, benzene ring H) 7.06–7.75 (2H, br, NH$_2$) 8.12–8.64 (2H, br, NH$_2$)

In the same way, 3-amino-5-benzyloxy-2-pentenethioamide (yield 48.3%) was obtained.

Melting point: 93° to 94° C. (chloroform-hexane)

IR spectrum (KBr cm$^{-1}$): 330–3350, 3200

NMR spectrum (CDCl$_3$): δppm 2.40 (2H, t, J=6.0 Hz, CH$_2$) 3.65 (2H, t, J=6.0 Hz, CH$_2$) 4.47 (2H, s, CH$_2$) 5.00 (1H, bs, CH) 5.95 (2H, br, NH$_2$, disappeared by D$_2$O) 7.24 (5H, s, benzene ring H) 8.02–8.41 (2H, br, NH$_2$, disappeared by D$_2$O)

In the same way, 3-amino-6-benzyloxy-2-hexenethioamide (57.3%) was obtained.

IR spectrum (neat cm$^{-1}$): 3450, 3360, 3330, 1600

NMR spectrum (CDCl$_3$): δppm 1.45–2.44 (4H, m, CH$_2$×2) 3.48 (2H, t, J=6.0 Hz, CH$_2$) 4.47 (2H, s, CH$_2$) 5.05 (1H, CH) 6.09 (2H, bs, NH$_2$) 7.38 (5H, s, benzene ring H) 7.60–8.87 (2H, br, NH$_2$)

REFERENTIAL EXAMPLE 5

Production of 5-amino-3-benzyloxymethylisothiazole

In a stream of argon, 182 ml of dry methanol, 191 ml of dry ether and 38.5 g (0.279 mole) of potassium carbonate were added to 31.0 g (0.140 mole) of 3-amino-4-benzyloxy-2-butenethioamide obtained in Referential Example 4, and under heating and reflux, a solution of 26.6 g (0.209 mole) of iodine in dry ether 191 ml was added droopwise to the mixture. Then, the mixture was refluxed for 1.5 hours, and 130 ml of dry ether containing 17.7 g (0.140 mole) of iodine was added dropwise under reflux. After cooling, water was added, and the mixture was extracted with ethyl acetate. The ethyl acetate layer was washed successively with water, an aqueous solution of sodium thiosulfate and a saturated aqueous solution of sodium chloride, and dried over anhydrous magnesium sulfate. The solvent was evaporated under reduced pressure. The resulting 5-amino-3-benzyloxymethyl isothiazole was subjected to silica gel column chromatography, and the column was eluted with chloroform/methanol (500/2) to give 25.5 g (83.0%) of a brown oily substance.

IR spectrum (neat cm$^{-1}$): 3450, 3320, 3200

NMR spectrum (CDCl$_3$): δppm 4.30–4.95 (2H, br, NH$_2$) 4.41 (2H, s, CH$_2$) 4.51 (2H, s, CH$_2$) 6.29 (1H, s, CH) 7.26 (5H, s, benzene ring H)

In the same way, 5-amino-3-(2-benzyloxyethyl)isothiazole (yield 100%) was obtained.

IR spectrum (neat cm$^{-1}$): 3450, 3320, 3200

NMR spectrum (CDCl$_3$): δppm 2.92 (2H, t, J=6.0 Hz, CH$_2$) 3.79 (2H, t, J=6.0 Hz, CH$_2$) 4.30–4.69 (2H, br, NH$_2$, disappeared by D$_2$O) 4.51 (2H, s, CH$_2$) 6.91 (1H, s, CH) 7.29 (5H, s, benzene ring H)

In the same way, 5-amino-3-(3-benzyloxypropyl)isothiazole was obtained (yield 96.7%).

IR spectrum (neat cm$^{-1}$): 3450, 3350, 3200

NMR spectrum (CDCl$_3$): δppm 2.00 (2H, quin, J=7.0 Hz, CH$_2$) 2.70 (2H, t, J=7.0 Hz, CH$_2$) 3.49 (2H, t, J=7.0 Hz, CH$_2$) 4.30–4.98 (2H, br, NH$_2$) 4.46 (2H, s, CH$_2$) 6.01 (1H, s, CH) 7.28 (5H, s, benzene ring H)

EXAMPLE 1

Production of ethyl 3-benzyloxymethyl-6-methyl-4-(3-nitrophenyl)-4,7-dihydroisothiazolo[5,4-b]pyridine-5-carboxylate 25.7 g (0.116 mole) of 5-amino-3-benzyloxymethylisothiazole obtained in Referential Example 5 and 30.4 g (0.116 mole) of ethyl 3-(3-nitrobenzylidene)acetoacetate were dissolved in 231 ml tert-butanol, and reacted in an argon stream at about 85° C. for 20 hours. The above acetoacetate compound was further added in an amount of 10 g (38.0 mM), and the reaction as carried out at the same temperature as above for 22 hours. After cooling, the solvent was evaporated under reduced pressure. The residue was acidified with 10% hydrochloric acid, and extracted with ethyl acetate. The ethyl acetate layer was washed successively with a saturated aqueous solution of sodium hydrogen carbonate, water and a saturated aqueous solution of sodium chloride, and dried over anhydrous magnesium sulfate. The solvent was evaporated under reduced pressure. The residue was subjected to silica gel column chromatography, and the column was eluted with chloroform/methanol (200/1) to give a pale brown jelly-like product. Recrystallization of the jelly-like product from chloroform/hexane to give 5.83 g (10.8%) of the captioned compound as colorless needles having a melting point of 153° to 154° C.

IR spectrum (KBr cm$^{-1}$): 3280, 1695

NMR spectrum (CDCl$_3$): δppm 1.17 (3H, t, J=7.0 Hz, CH$_3$) 2.36 (3H, s, CH$_3$) 4.04 (2H, q, J=7.0 Hz, CH$_2$) 4.22 (2H, bs, CH$_2$) 4.43 (2H, s, CH$_2$) 5.45 (1H, s, CH) 7.00–8.32 (9H, m, benzene ring H)

In the same manner as above, ethyl 3-(2-beznyloxyethyl)-6-methyl-4-(3-nitrophenyl)-4,7-dihydroisothiazolo[5,4-b]pyridine-5-carboxylate was obtained (yield 16.3%).

IR spectrum (neat cm$^{-1}$): 3300, 1680

NMR spectrum (CDCl$_3$): δppm 1.22 (3H, t, J=7.0 Hz, CH$_3$) 2.43 (3H, t, s, CH$_3$) 2.72 (2H, m, CH$_2$) 3.66 (2H, m, CH$_2$) 4.07 (2H, q, J=7.0 Hz, CH$_2$) 4.43 (2H, s, CH$_2$) 5.37 (1H, s, CH) 6.68–8.20 (10H, m, benzene ring H)

In the same manner as above, ethyl 3-(3-benzyloxypropyl)-6-methyl-4-(3-nitrophenyl)-4,7-dihydroisothiazolo[5,4-b]pyridine-5-carboxylate was obtained (yield 8.4%).

Melting point: 109°–110° C.

IR spectrum (KBr cm$^{-1}$): 3260, 1690

NMR spectrum (CDCl$_3$): δppm 1.21 (3H, t, J=7.0 Hz, CH$_3$) 1.51–2.85 (4H, m, CH$_2$×2) 2.89 (3H, s, CH$_3$) 3.42 (2H, t, J=7.0 Hz, CH$_2$) 4.11 (2H, q, J=7.0 Hz, CH$_2$) 4.05 (2H, s, CH$_2$) 5.31 (1H, s, CH) 7.18–8.27 (5H, m, benzene ring H, NH) 7.28 (5H, s, benzene ring H)

EXAMPLE 2

Production of ethyl 3-hydroxymethyl-6-methyl-4-(3-nitrophenyl)-4,7-dihydroisothiazolo[5,4-b]pyridine-5-carboxylate In a stream of argon, 1.17 g (25.2 mM) of the ethyl 3-benzyloxymethyl-6-methyl-4-(3-nitrophenyl)-4,7-dihydroisothiazolo[5,4-b]pyridine-5-carboxylate obtained in Example 1 was dissolved in 6 ml of dry methylene chloride. Under ice cooling, 6 ml of methyl sulfide was added. Furthermore, 3.1 ml of boron trifluoride etherate was added dropwise, and the mixture was stirred at the above temperature for 30 minutes. Then, the temperautre was returned to room temperaure, and the mixture was furhter stirred overnight. The reaction mixture was poured into ice water, alkalified by addition of a saturated aqueous solution of sodium hydrogen carbonate, and extracted with ethyl acetate. The ethyl acetate layer was washed with water and a saturated aqueous soution of sodium chloride and dried over anhydrous magnesium sulfate. The solvent was then evaporated under reduced pressure to give crystals. Recrystallization of the crystals from chloroform-hexane gave 891 mg (94.2%) as a colorless powder having a melting point of 202° to 205° C.

IR spectrum (KBr cm$^{-1}$): 3240, 1695, 1675

NMR spectrum (CDCl$_3$+CD$_3$OD): δppm 1.20 (3H, t, J=7.0 Hz, CH$_3$) 2.40 (3H, s, CH$_3$) 4.08 (2H, q, J=7.0 Hz, CH$_2$) 4.45 (2H, s, CH$_2$) 5.48 (1H, s, CH) 7.26–8.20 (5H, m, benzene ring H, NH)

In a similar manner, ethyl 3-(2-hydroxyethyl)-6-methyl-4-(3-nitrophenyl)-4,7-dihydroisothiazolo[5,4-b]pyridine-5-carboxylate was obtained (yield 100%).

IR spectrum (neat cm$^{-1}$): 3500–3300, 1690, 1670

NMR spectrum (CDCl$_3$): δppm 1.23 (3H, t, J=7.0 Hz, CH$_3$) 2.46 (3H, s, CH$_3$) 2.48–3.20 (3H, m, CH$_2$OH, 1H, disappeared by D$_2$O) 3.65–4.23 (2H, m, CH$_2$) 4.12 (2H, q, J=7.0 Hz, CH$_2$) 5.30 (1H, s, CH) 6.78 (1H, bs, NH, disappeared by D$_2$O) 7.16–8.13 (4H, m, benzene ring H)

In a similar manner, ethyl 3-(3-hydroxypropyl)-6-methyl-4-(3-nitrophenyl)-4,7-dihydroisothiazolo[5,4-b]pyridine-5-carboxylate was obtained (yield 100%).

IR spectrum (neat cm$^{-1}$): 3300, 1690, 1680

NMR spectrum (CDCl$_3$): δppm 1.24 (3H, t, J=7.0 Hz, CH$_3$) 1.49–2.09 (4H, m, CH$_2$×2) 2.40 (3H, s, CH$_3$) 3.42–3.81 (1H, br, OH) 3.61 (2H, t, J=5.0 Hz, CH$_2$) 4.13 (2H, q, J=7.0 Hz, CH$_2$) 5.31 (1H, s, CH) 7.40–8.42 (5H, m, benzene ring H, NH)

EXAMPLE 3

Production of ethyl 3-[N-(2-(3,4-dimethoxyphenyl)ethyl)-N-methylaminomethyl]-6-methyl-4-(3-nitrophenyl)-4,7-dihydroisothiazolo[5,4-b]pyridine-5-carboxylate In an argon stream, 630 mg (1.68 mM) of ethyl 3-hydroxymethyl-6-methyl-4-(3-nitrophenyl)-4,7-dihydroisothiazolo[5,4-b]pyridine-5-carboxylate obtained in Example 2 was dissolved in 6 ml of anhydrous tetrahydrofuran, and under ice cooling, 0.62 ml (4.45 mM) of triethylamine was added. A solution of 0.26 ml (3.36 mM) of methanesulfonyl chloride in 2 ml of anhydrous tetrahydrofuran was added dropwise, and reacted at the above temperature for 45 minutes. Water (6 ml) was added to the reaction mixture, and the mixture was stirred for 10 minutes. The mixture was then poured into 10% HCl-ice, and extracted with methylene chloride. The methylene chloride layer was washed with water and a saturated aqueous solution of sodium chloride, and dried over anhydrous magnesium sulfate. The solvent was evaporated under reduced pressure to give 927 mg of crude ethyl 3-methanesulfonyloxymethyl-6-methyl-4-(3-nitrophenyl)-4,7-dihydroisothiazolo[5,4-b]pyridine-5-carboxylate as a pale yellow jelly-like product.

N-methylhomoveratrylamine (1.65 g; 8.40 mM) was added to the crude jelly-like product, and the mixture was stirred at about 80° C. for 4 hours in an argon stream. After cooling, the reaction mixture was mixed with 10% hydrochloric acid and extracted with ethyl acetate. The ethyl acetate layer was washed successively with water, a saturated aqueous solution of sodium hydrogen carbonate, water and a saturated aqueous solution of sodium chloride, and dried over anhydrous sodium sulfate. The solvent was evaporated under reduced pressure. The resulting ethyl 3-[N-(2-(3,4-dimethoxyphenyl)ethyl)-N-methylaminomethyl]-6-methyl-4-(3-nitrophenyl)-4,7-dihydroisothiazolo[5,4-b]pyridine-5-carboxylate was subjected to silica gel column chromatography, and the column was eluted with a 3:1 mixture of hexane and ethyl acetate to give 555 mg (59.8%) of a pale yellow jelly-like product.

IR spectrum (neat cm$^{-1}$): 3350, 1695

NMR spectrum (CDCl$_3$): $\delta$ppm 1.21 (3H, t, J=7.0 Hz, CH$_3$) 2.05–2.90 (4H, m, CH$_2$×2) 2.20 (3H, s, CH$_3$) 2.42 (3H, s, CH$_3$) 3.25 (2H, bs, CH$_2$) 3.82 (6H, s, OCH$_3$×2) 4.08 (2H, q, J=7.0 Hz, CH$_2$) 5.52 (1H, s, CH) 6.50–6.85 (3H, m, benzene ring H) 7.10–8.48 (5H, m, benzene ring H, NH)

EXAMPLES 4–52

The compounds shown in Table 3 were produced in the same way as in Example 3. Table 4 gives IR and NMR spectral data of the compounds produced in Examples 4 to 52.

TABLE 3

| Example | R$^1$ | R$^2$ | m | Yield (%) | Appearance |
|---|---|---|---|---|---|
| 4 | Et | 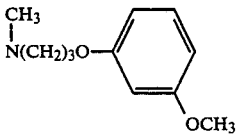 | 1 | 55.0 | Pale yellow viscous product |
| 5 | Et | 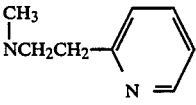 | 1 | 68.6 | Pale yellow viscous product |
| 6 | Et | 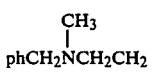 | 1 | 51.9 | Pale brown viscous product |
| 7 | phCH$_2$NCH$_2$CH$_2$ (CH$_3$) | H | 1 | 5.9 | Yellow needles (mp 152–154° C.) |
| 8 | phCH$_2$NCH$_2$CH$_2$ (CH$_3$) | 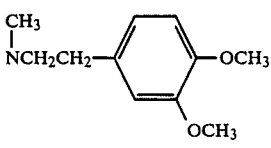 | 1 | 76.8 | Pale brown amorphous powder |
| 9 | phCH$_2$NCH$_2$CH$_2$ (CH$_3$) | 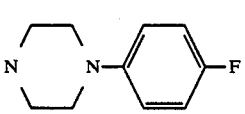 | 1 | 59.2 | Pale brown amorphous powder |

TABLE 3-continued

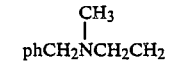

| Example | R¹ | R² | m | Yield (%) | Appearance |
|---|---|---|---|---|---|
| 10 | CH₃<br>│<br>phCH₂NCH₂CH₂ | 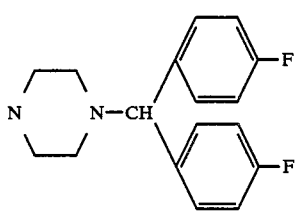 | 1 | 62.9 | Pale brown amorphous powder |
| 11 | Et | 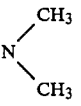 | 2 | 78.8 | Yellow powder<br>(mp 114–117° as hydrochloride) |
| 12 | Et | 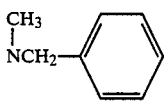 | 2 | 53.4 | Yellowish amorphous powder |
| 13 | Et | 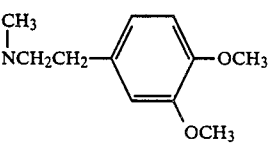 | 2 | 37.4 | Pale yellow amorphous powder |
| 14 | Et | 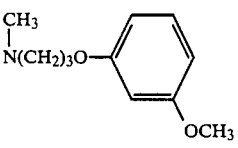 | 2 | 38.6 | Pale brown amorphous powder |
| 15 | Et | 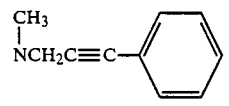 | 2 | 29.0 | Yellow amorphous powder |
| 16 | Et | 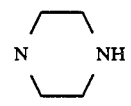 | 2 | 70.0 | Yellow amorphous powder |
| 17 | Et | 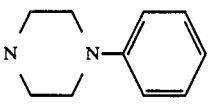 | 2 | 92.2 | Pale yellow powder<br>(mp 175–177° C.) |
| 18 | Et | 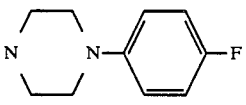 | 2 | 89.6 | Pale yellow amorphous powder |
| 19 | Et | 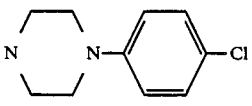 | 2 | 62.5 | Colorless powder (mp 190–192°) |

TABLE 3-continued

Structure: R¹OOC and (CH₂)ₘR² substituents on a dihydropyridine fused with isothiazole, with 3-nitrophenyl and CH₃ groups.

| Example | R¹ | R² | m | Yield (%) | Appearance |
|---------|----|----|---|-----------|------------|
| 20 | Et | 4-(2,4-dimethylphenyl)piperazin-1-yl | 2 | 62.3 | Pale yellow granular crystals (mp 188–189.5°) |
| 21 | Et | 4-(2,3-dimethylphenyl)piperazin-1-yl | 2 | 65.0 | Pale yellow prisms (mp 214–215.5°) |
| 22 | Et | 4-(2-methoxyphenyl)piperazin-1-yl | 2 | 61.0 | Yellow amorphous powder |
| 23 | Et | 4-(4-methoxyphenyl)piperazin-1-yl | 2 | 67.2 | Yellowish prisms (mp 145–148°) |
| 24 | Et | 4-(2-ethoxyphenyl)piperazin-1-yl | 2 | 65.3 | Yellowish powder (mp 178–181°) |
| 25 | Et | 4-(3,4-dimethoxyphenyl)piperazin-1-yl | 2 | 73.3 | Yellow needles (mp 167–168° C.) |
| 26 | Et | 4-(4-trifluoromethylphenyl)piperazin-1-yl | 2 | 64.0 | Yellowish powder (mp 186–188° C.) |
| 27 | Et | 4-(4-cyanophenyl)piperazin-1-yl | 2 | 61.7 | Pale yellow powder (mp 218–220°) |
| 28 | Et | 4-(4-aminophenyl)piperazin-1-yl | 2 | 69.8 | Brown amorphous powder |
| 29 | Et | 4-(4-nitrophenyl)piperazin-1-yl | 2 | 60.4 | Yellow powder (mp 232–240°) |

TABLE 3-continued

Structure: 4-(3-nitrophenyl) dihydropyridine fused isothiazole with R¹OOC-, CH₃-, and -(CH₂)ₘR² substituents

| Example | R¹ | R² | m | Yield (%) | Appearance |
|---------|-----|-----|---|-----------|------------|
| 30 | Et | piperazinyl-(2-pyridyl) | 2 | 71.4 | Pale yellow granular crystals (mp 175–177°) |
| 31 | Et | 4-methylpiperazinyl | 2 | 53.0 | Pale yellow powder (mp 186–188°) |
| 32 | Et | 4-(2-hydroxyethyl)piperazinyl | 2 | 77.0 | Pale yellow amorphous powder |
| 33 | Et | 4-cyclohexylpiperazinyl | 2 | 58.0 | Pale yellow powder [mp 147–150° (decomp.) as hydrochloride] |
| 34 | Et | 4-benzylpiperazinyl | 2 | 96.0 | Pale yellow powder (mp 129–133° as hydrochloride) |
| 35 | Et | 4-(2-furoyl)piperazinyl | 2 | 54.6 | Yellowish powder (mp 150–154° hydrochloride) |
| 36 | Et | 4-[bis(4-fluorophenyl)methyl]piperazinyl | 2 | 86.5 | Pale yellow amorphous powder |
| 37 | phCH₂N(CH₃)CH₂CH₂ | 4-(4-fluorophenyl)piperazinyl | 2 | 97.0 | Pale yellow amorphous powder |
| *38 | CH₃ | 4-phenylpiperazinyl | 2 | 45.7 | Yellowish powder (mp 109–112°) |
| *39 | CH₃ | 4-(4-fluorophenyl)piperazinyl | 2 | 51.1 | Yellowish powder (mp 112–114°) |

TABLE 3-continued
| Example | R¹ | R² | m | Yield (%) | Appearance |
|---|---|---|---|---|---|
| 40 | Et |  | 2 | 41.1 | Pale yellow powder (mp 183–185°) |
| 41 | Et |  | 2 | 56.1 | Pale yellow powder (mp 152–154°) |
| 42 | Et |  | 2 | 58.9 | Pale yellow powder (mp 89–92°) |
| 43 | Et | 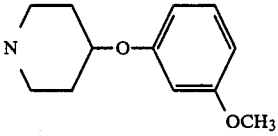 | 2 | 78.9 | Pale yellow amorphous powder |
| 44 | Et | 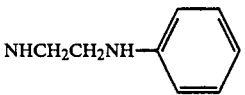 | 2 | 66.9 | Pale yellow powder |
| 45 | Et | 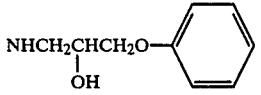 | 2 | 67.0 | Yellow amorphous powder (mp 57–60°) |
| 46 | Et | 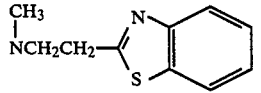 | 2 | 37.9 | Pale yellow powder (mp 157–160°) |
| 47 | Et | 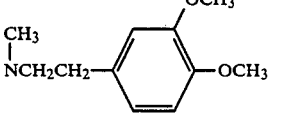 | 2 | 40.0 | Yellow amorphous powder |
| 48 | Et | 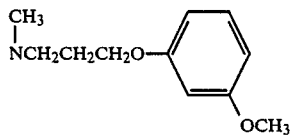 | 3 | 44.3 | Pale yellow viscous product |
| 49 | Et |  | 3 | 72.7 | Pale yellow viscous product |

TABLE 3-continued

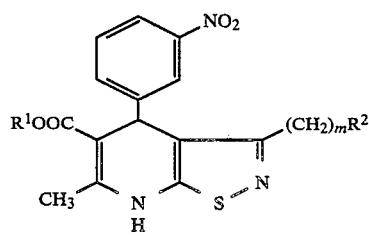

| Example | R¹ | R² | m | Yield (%) | Appearance |
|---------|----|----|---|-----------|------------|
| 50 | Et | CH₃ \| NCH₂C≡C—(phenyl) | 3 | 28.3 | Pale yellow amorphous powder |
| 51 | Et | (piperazinyl)N—(4-F-phenyl) | 3 | 58.5 | Pale yellow amorphous powder |
| 52 | Et | (piperazinyl)NCH(4-F-phenyl)(4-F-phenyl) | 3 | 67.2 | Pale brown amorphous powder |

*The nitro group is substituted at the ortho-position.

TABLE 4

| Example | IR $\nu$ (cm$^{-1}$) | NMR (CDCl$_3$) $\delta$ ppm |
|---------|----------------------|------------------------------|
| 4 | (neat) 3300, 1690, 1660 | 1.22(3H, t, J=7.0Hz, CH$_3$), 2.15(6H, s, CH$_3 \times 2$), 2.42(3H, s, CH$_3$), 3.26(2H, s, CH$_2$), 4.13(2H, q, J=7.0Hz, CH$_2$), 5.11(1H, s, CH), 7.34–8.25(4H, m, benzene ring H), 8.93(1H, bs, NH) |
| 5 | (neat) 3300, 1690, 1670 | 1.18(3H, t, J=7.0Hz, CH$_3$), 1.69–2.84(4H, m, CH$_2 \times 2$), 2.18, 2.37(each, 3H, s, CH$_3$), 3.18(2H, s, CH$_2$), 3.76(3H, s, OCH$_3$), 3.88(2H, t, J=5.0Hz, CH$_2$), 3.99(2H, q, J=7.0Hz, CH$_2$), 5.66(1H, s, CH), 6.28–6.68(3H, m, benzene ring H), 7.02–8.18(6H, m, benzene ring H, NH) |
| 6 | (neat) 3300, 1690, 1670 | 1.20(3H, t, J=7.0Hz, CH$_3$), 2.23, 2.41(each, 3H, s, CH$_3$), 2.52–3.07(4H, m, CH$_2 \times 2$), 3.23(2H, bs, CH$_2$), 4.15(2H, q, J=7.0Hz, CH$_2$), 5.41(1H, s, CH), 7.01–8.72(9H, m, benzene ring H and pyridine ring H, NH) |
| 7 | (KBr) 3250, 1685 | 2.10, 2.25, 2.45(each, 3H, s, CH$_3$), 2.65(2H, t, J=5.0Hz, CH$_2$), 3.53(2H, s, CH$_2$), 4.03–4.30(2H, m, CH$_2$), 5.27(1H, s, CH), 6.65–8.11(5H, m, benzene ring H, NH), 7.29(5H, s, benzene ring H) |
| 8 | (KBr) 3300, 1690, 1670 | 2.20(6H, s, CH$_3 \times 2$), 2.30–2.75(2H, m, CH$_2$), 2.42(2H, s, CH$_2$), 3.22(2H, d, J=3.8Hz, CH$_2$), 3.50(2H, s, CH$_2$), 3.82(6H, s, OCH$_3 \times 2$), 4.17(2H, t, J=5.0Hz, CH$_2$), 5.30(1H, s, CH), 6.35–8.18(8H, m, benzene ring H, NH) |
| 9 | (KBr) 3300, 1690, 1670 | 2.28, 2.45(each, 3H, s, CH$_3$), 2.34–3.38(8H, m, CH$_2 \times 2$), 3.27(2H, d, J=3.8Hz, CH$_2$), 3.46(2H, s, CH$_2$), 4.15(2H, t, J=5.0Hz, CH$_2$), 5.70(1H, s, CH), 6.73–8.23(9H, m, benzene ring H, NH), 7.23(5H, s, benzene ring H) |
| 10 | (KBr) 3300, 1690, 1670 | 2.01–2.51(8H, m, CH$_2 \times 4$), 2.26, 2.41(each, 3H, s, CH$_3$), 2.68(2H, t, J=5.0Hz, CH$_2$), 3.17–3.25(2H, bs, CH$_2$), 3.55(2H, s, CH$_2$), 4.05–4.29(3H, m, CH$_2$, CH), 5.65(1H, s, CH), 6.57–8.17(5H, m, benzene ring H, NH), 7.28(8H, s, benzene ring H) |
| 11 | (KBr) 3400, 1690, 1670 | 1.25(3H, t, J=7.0Hz, CH$_3$), 2.20(6H, s, CH$_3 \times 2$), 2.45(3H, s, CH$_3$), 4.13(2H, q, J=7.0Hz, CH$_2$), 5.36(1H, s, CH), 6.82(1H, bs, NH), 7.30–8.21(4H, m, benzene ring H) |
| 12 | (KBr) 3300, 1690, 1665 | 1.25(3H, t, J=7.0Hz, CH$_3$), 1.90–2.85(4H, m, CH$_2 \times 2$), 2.17(3H, s, CH$_3$), 2.54(3H, s, CH$_3$), 3.54(2H, s, CH$_2$), 4.12(2H, q, J=7.0Hz, CH$_2$), 5.30(1H, s, CH), 6.78(1H, bs, NH), 7.10–8.17(4H, m, benzene ring H), 7.27(5H, s, benzene ring H) |
| 13 | (KBr) 3330, 1690 | 1.25(3H, t, J=7.0Hz, CH$_3$), 2.26, 2.43(each, 3H, s, CH$_3$), 2.13–2.90(8H, m, CH$_2 \times 4$), 3.87(6H, s, OCH$_3 \times 2$), 4.11(2H, q, J=7.0Hz, CH$_2$), 5.35(1H, s, CH), 6.62–8.15(8H, m, benzene ring H, NH) |

TABLE 4-continued

| Example | IR ν (cm⁻¹) | NMR (CDCl₃) δ ppm |
|---|---|---|
| 14 | (KBr) 3600–3200, 1690, 1660 | 1.27(3H, t, J=7.0Hz, CH₃), 1.66–2.02(2H, m, CH₂), 2.05–2.67 (6H, m, CH₂×3), 2.12, 2.43(each, 3H, s, CH₃), 3.82(3H, s, OCH₃), 3.92(2H, t, J=5.2Hz, CH₂), 4.12(2H, q, J=7.0Hz, CH₂), 5.37(1H, s, CH), 6.38–6.75(3H, m, benzene ring H), 7.15–8.26(5H, m, benzene ring H, NH) |
| 15 | (KBr) 3250, 1690, 1665 | 1.22(3H, t, J=7.0Hz, CH₃), 2.25–2.95(4H, m, CH₂×2), 2.32, 2.43(each, 3H, s, CH₃), 3.48(2H, s, CH₂), 4.08(2H, t, J=7.0Hz, CH₂), 5.35(1H, s, CH), 7.14–8.18(9H, m, benzene ring H) |
| 16 | (KBr) 3200, 1690, 1670 | 1.25(3H, t, J=7.0Hz, CH₃), 1.80–3.09(12H, m, CH₂×6), 2.45(3H, s, CH₃), 3.50(1H, s, NH), 4.13(2H, q, J=7.0Hz, CH₂), 5.36(1H, s, CH), 7.18(1H, bs, NH), 7.00–8.32(4H, m, benzene ring H) |
| 17 | (KBr) 3300, 1690, 1670 | 1.23(3H, t, J=7.0Hz, CH₃), 2.16–3.34(12H, m, CH₂×6), 2.42(3H, s, CH₃), 4.11(2H, q, J=7.0Hz, CH₂), 5.36(1H, s, CH), 6.67–8.20(10H, m, benzene ring H, NH) |
| 18 | (KBr) 3300, 1690, 1670 | 1.23(3H, t, J=7.0Hz, CH₃), 2.23–3.24(12H, m, CH₂×6), 2.24(3H, s, OCH₃), 4.11(2H, q, J=7.0Hz, CH₃), 5.37(1H, bs, CH), 6.61–8.18(8H, m, benzene ring H, NH) |
| 19 | (KBr) 3310, 1690, 1670 | 1.27(3H, t, J=7.0Hz, CH₃), 2.25–3.26(12H, m, CH₂×6), 2.47(3H, s, CH₃), 4.14(2H, q, J=7.0Hz, CH₂), 5.40(1H, s, CH), 6.67–8.23(8H, m, benzene ring H), 6.79(1H, bs, NH) |
| 20 | (KBr) 3350, 1690, 1670 | 1.27(3H, t, J=7.0Hz, CH₃), 2.05–3.25(12H, m, CH₂×6), 2.19, 2.25, 2.45(each, 3H, s, CH₃), 4.15(2H, q, J=7.0Hz, CH₂), 5.38(1H, s, CH), 6.58–8.20(7H, m, benzene ring H) |
| 21 | (KBr) 3320, 1695, 1675 | 1.27(3H, t, J=7.0Hz, CH₃), 2.05–3.15(12H, m, CH₂×6), 2.22, 2.28, 2.46(each, 3H, s, CH₃), 4.15(2H, q, J=7.0Hz, CH₂), 5.41(1H, s, CH), 6.75(1H, bs, NH), 6.82–8.25(7H, m, benzene ring H) |
| 22 | (KBr) 3300, 1690, 1670 | 1.26(3H, t, J=7.0Hz, CH₃), 2.33–3.35(12H, m, CH₂×6), 2.43 (3H, s, CH₃), 3.86(3H, s, OCH₃), 4.13(2H, q, J=7.0Hz, CH₂), 5.36(1H, s, CH), 6.74–8.23(9H, m, benzene ring H, NH) |
| 23 | (KBr) 3310, 1690, 1670 | 1.26(3H, t, J=7.0Hz, CH₃), 2.05–3.25(12H, m, CH₂×6), 2.45 (3H, s, CH₃), 3.77(3H, s, OCH₃), 4.15(2H, q, J=7.0Hz, CH₂), 5.48(1H, s, CH), 6.70(1H, bs, NH), 6.74–8.20(8H, m, benzene ring H) |
| 24 | (KBr) 3300, 1690, 1670, 1640, 1610 | 1.26, 1.46(each, 3H, t, J=7.0Hz, CH₃), 2.38–3.26(12H, m, CH₂×6), 2.46(3H, s, CH₃), 4.06, 4.13(each, 2H, q, J=7.0Hz, CH₂), 5.39(1H, s, CH), 6.67(1H, s, NH), 6.75–8.30(8H, m, benzene ring H) |
| 25 | (KBr) 3300, 1690, 1670, 1640, 1610 | 1.25(3H, t, J=7.0Hz, CH₃), 2.20–3.25(12H, m, CH₂×6), 2.45(3H, s, CH₃), 3.85, 3.88(each, 3H, s, OCH₃), 4.14(2H, q, J=7.0Hz, CH₂), 5.39(1H, s, CH), 6.30–8.28(8H, m, benzene ring H, NH) |
| 26 | (KBr) 3350, 1690, 1670, 1640, 1610 | 1.25 (3H, t, J=7.0Hz, CH₃), 2.22–3.48(12H, m, CH₂×6), 2.46(3H, s, CH₃), 4.13(2H, q, J=7.0Hz, CH₂), 5.38(1H, s, CH), 6.57–8.20 (9H, m, benzene ring H, NH) |
| 27 | (KBr) 3350, 2200, 1690, 1670, 1600 | 1.25(3H, t, J=7.0Hz, CH₃), 2.10–3.29(12H, m, CH₂×6), 2.45(3H, s, CH₃), 4.13(2H, q, J=7.0Hz, CH₂), 5.38(1H, s, CH), 6.58–8.24(9H, m, benzene ring H, NH) |
| 28 | (KBr) 3350, 3250, 1690, 1670 | 0.65–3.40(2H, b, NH₂), 1.25(3H, t, J=7.0Hz, CH₃), 2.18–3.25 (12H, m, CH₂×6), 2.45(3H, s, CH₃), 4.13(2H, q, J=7.0Hz, CH₂), 5.38(1H, s, CH), 6.45–8.28(9H, m, benzene ring H, NH) |
| 29 | (KBr) 3300, 1690, 1670 | 1.25(3H, t, J=7.0Hz, CH₃), 2.30–3.55(12H, m, CH₂×6), 2.46(3H, s, CH₃), 4.13(2H, q, J=7.0Hz, CH₂), 5.38(1H, s, CH), 6.55–8.34(9H, m, benzene ring H, NH) |
| 30 | (KBr) 3320, 1695, 1675 | 1.27(3H, t, J=7.0Hz, CH₃), 2.00–2.95(8H, m, CH₂×4), 2.45(3H, s, CH₃), 3.30–3.75(4H, m, CH₂×2), 4.14(2H, q, J=7.0Hz, CH₂), 5.40(1H, s, CH), 7.20(1H, s, NH), 6.50–8.30(8H, m, benzene ring H, pyridine ring H) |
| 31 | (KBr) 3300, 1690, 1670 | 1.26(3H, t, J=7.0Hz, CH₃), 2.00–2.90(12H, m, CH₂×6), 2.28 2.44(each, 3H, s, CH₃), 4.13(2H, q, J=7.0Hz, CH₂), 5.36(1H, s, CH), 7..08(1H, bs, NH), 7.20–8.20(4H, m, benzene ring H) |
| 32 | (KBr) 3400, 3250, 1690, 1665 | 1.26(3H, t, J=7.0Hz, CH₃), 1.50–3.05(15H, m, CH₂×7, OH), 2.45(3H, s, CH₃), 3.62(2H; m, CH₂), 4.13(2H, q, J=7.0Hz, CH₂), 5.37(1H, s, CH), 6.99(1H, bs, NH), 7.16–8.24(4H, m, benzene ring H) |
| 33 | (neat) 3350, 1690, 1670 | 0.75–3.26(11H, m, CH₂×5, CH), 1.18(3H, t, J=7.0Hz, CH₃), 2.29(3H, s, CH₃), 4.01(2H, q, J=7.0Hz, CH₂), 5.20(1H, s, CH), 7.15–8.34(4H, m, benzene ring H, NH) |
| 34 | (KBr) 3300, 2825, 1690, 1670 | 1.24(3H, t, J=7.0Hz, CH₃), 2.12–2.96(12H, m, CH₂×6), 2.43 (3H, s, CH₃), 3.48(2H, s, CH₂), 4.11(2H, q, J=7.0Hz, CH₂), 5.32(1H, s, CH), 6.92(1H, s, NH), 6.78–8.30(9H, m, benzene ring H) |
| 35 | (KBr) 3400, 3250, 1690, 1665 | 1.26(3H, t, J=7.0Hz, CH₃), 2.00–3.92(12H, m, CH₂×6), 2.45 (3H, s, CH₃), 4.13(2H, q, J=7.0Hz, CH₂), 5.36(1H, s, CH), 6.50(1H, bs, NH), 6.84–8.22(7H, m, benzene ring H, furane ring H) |
| 36 | (KBr) 3300, 1695, 1670 | 1.22(3H, t, J=7.0Hz, CH₃), 2.04–2.71(12H, m, CH₂×6), 2.37(3H, s, CH₃), 4.12(2H, q, J=7.0Hz, CH₂), 4.20, 5.32 (each, 1H, s, CH), 6.67–8.17(13H, m, benzene ring H, NH) |

TABLE 4-continued

| Example | IR ν (cm⁻¹) | NMR (CDCl₃) δ ppm |
|---|---|---|
| 37 | (KBr) 3300, 1690, 1670 | 2.02, 2.21(each, 3H, s, CH₃), 2.12–3.15(12H, m, CH₂×6), 3.20–3.74(2H, m, CH₂), 3.32(2H, s, CH₂), 4.01(2H, t, J=5.0Hz, CH₂), 5.19(1H, s, CH), 6.45–8.01(14H, m, benzene ring H, NH) |
| 38 | (KBr) 3400, 1700, 1640 | 2.47(3H, s, CH₃), 2.40–3.32(12H, m, CH₂×6), 3.74(3H, s, CH₃), 5.27(1H, s, CH), 6.75–7.48(9H, m, benzene ring H) |
| 39 | (KBr) 3400, 1700, 1640 | 2.47(3H, s, CH₃), 2.40–3.25(12H, m, CH₂×6), 3.75(3H, s, CH₃), 5.27(1H, s, CH), 6.00(1H, bs, NH), 6.75–7.45(8H, m, benzene ring H) |
| 40 | (KBr) 3245, 1680 | 1.26 (3H, t, J=7.0Hz, CH₃), 1.40–3.00(12H, m, CH₂×6), 2.46 (3H, s, CH₃), 4.14(2H, q, J=7.0Hz, CH₂), 5.37(1H, s, CH), 7.03(1H, bs, NH), 7.15–8.18(4H, m, benzene ring H) |
| 41 | (KBr) 3310, 1675 | 1.25 (3H, t, J=7.0Hz, CH₃), 1.38–2.85(14H, m, CH₂×7), 2.45 (3H, s, CH₃), 4.12(2H, q, J=7.0Hz, CH₂), 5.37(1H, s, CH), 6.97(1H, bs, NH), 7.20–8.23(4H, m, benzene ring H) |
| 42 | (KBr) 3275, 1685, 1665 | 1.26(3H, t, J=7.0Hz, CH₃), 2.05–2.95(8H, m, CH₂×4), 2.45(3H, s, CH₃), 3.55–4.85(4H, m, CH₂×2), 4.15(2H, q, J=7.0Hz, CH₂), 5.38(1H, s, CH), 6.88(1H, bs, NH), 7.25–8.20(4H, m, benzene ring H) |
| 43 | (KBr) 3400, 2950, 1690, 1670 | 1.25(3H, t, J=7.0Hz, CH₃), 1.40–3.50(13H, m, CH₂×6, CH), 2.45(3H, s, CH₃); 4.12(2H, q, J=7.0Hz, CH₂), 5.36(1H, s, CH), 6.83(1H, s, NH), 6.63–8.45(9H, m, benzene ring H) |
| 44 | (KBr) 3275, 1690, 1670 | 1.25(3H, t, J=7.0Hz, CH₃), 1.80–3.06(12H, m, CH₂×6), 2.45(3H, s, CH₃), 3.79(3H, s, OCH₃), 3.93–4.50(1H, b, CH), 4.13(2H, q, J=7.0Hz CH₂), 5.37(1H, s, CH), 6.30–8.19(9H, m, benzene ring H, NH) |
| 45 | (KBr) 3360, 1690, 1670 | 1.25(3H, t, J=7.0Hz, CH₃), 1.63(2H, bs, NH×2), 2.25–3.34(8H, m, CH₂×4), 2.44(3H, s, CH₃), 4.14(2H, q, J=7.0Hz, CH₂), 5.33(1H, s, CH), 6.46–8.18(9H, m, benzene ring H), 6.89(1H, bs, NH) |
| 46 | (KBr) 3400, 1690, 1665 | 1.25(3H, t, J=7.0Hz, CH₃), 1.58–2.25(3H, br, OH, NH×2), 2.25–3.13(6H, m, CH₂×3), 2.55(3H, s, CH₃), 3.96(3H, bs, CH₂, CH), 4.12(2H, q, J=7.0Hz, CH₂), 5.32(1H, s, CH), 6.77–8.24 (9H, m, benzene ring H) |
| 47 | (KBr) 3225, 1690 | 1.25(3H, t, J=8.0Hz, CH₃), 2.30, 2.45(each, 3H, s, CH₃), 2.55–2.90(6H, m, CH₂×3), 3.20(2H, t, J=6.0Hz, CH₂), 4.10(2H, q, J=8.0Hz, CH₂), 5.35(1H, s, CH), 6.80(1H, bs, NH), 7.35–8.05(8H, m, benzene ring H) |
| 48 | (neat) 3350, 1690, 1670 | 1.19(3H, t, J=7.0Hz, CH₃), 1.42–2.81(10H, m, CH₂×5), 2.20, 2.40 (each, 3H, s, CH₃), 3.82(6H, s, OCH₃×2), 4.04(2H, t, J=7.0Hz, CH₂), 5.30(1H, s, CH), 7.31–8.18(5H, m, benzene ring H, NH) |
| 49 | (neat) 3300, 1690, 1670 | 1.18(3H, t, J=7.0Hz, CH₃), 1.69–2.84(4H, m, CH₂×2), 2.18, 2.37(each, 3H, s, CH₃), 3.18(2H, s, CH₂), 3.76(3H, s, OCH₃), 3.88(2H, t, J=5.0Hz, CH₂), 3.99(2H, q, J=7.0Hz, CH₂), 5.56(1H, s, CH), 6.28–6.68(3H, m, benzene ring H), 7.02–8.18(6H, m, benzene ring H, NH) |
| 50 | (KBr) 3250, 1690, 1670 | 1.25(3H, t, J=7.0Hz, CH₃), 2.00–3.00(6H, m, CH₂×3), 2.33 (3H, s, CH₃), 2.45(3H, s, CH₃), 3.46(2H, s, CH₂), 4.08(2H, t, J=7.0Hz, CH₂), 5.35(1H, s, CH), 7.14–8.20(9H, m, benzene ring H) |
| 51 | (KBr) 3250, 1690, 1670, 1615 | 1.20(3H, t, J=7.0Hz, CH₃), 1.40–3.90(14H, m, CH₂×7), 2.43(3H, s, CH₃), 4.08(2H, q, J=7.0Hz, CH₂), 5.33(1H, s, CH), 6.74–8.23(9H, m, benzene ring H, NH) |
| 52 | (KBr) 3250, 1690, 1670 | 1.23(3H, t, J=7.0Hz, CH₃), 1.94–2.86(14H, m, CH₂×7), 2.33 (3H, s, CH₃), 4.10(2H, q, J=7.0Hz, CH₂), 4.20, 5.20(each, 1H, s, CH), 6.68–8.16(13H, m, benzene ring H, NH) |

EXAMPLE 53

Production of (+)-5-((S)-2-methoxy-2-phenyl)ethyl 3,6-dimethyl-4-(3-nitrophenyl)-4,7-dihydroisothiazolo[5,4-b]pyridine-5-carboxylate and (−)-5-((S)-2-methoxy-2-phenyl)ethyl 3,6-dimethyl-4-(3-nitrophenyl)-4,7-dihydroisothiazolo[5,4-b]pyridine-5-carboxylate Dry toluene (2 ml) containing 450 mg (1.17 mM) of t-butyl 3,6-dimethyl-4-(3-nitrophenyl)-4,7-dihydroisothiazolo[5,4-b]pyridine-5-carboxylate obtained from t-butyl 3-(3-nitrobenzylidene)acetoacetate and 5-amino-3-methylisothiazole was added to a solution of composed of 1 ml of 25% hydrobromic acid/acetic acid solution and 1 ml of dry toluene under ice cooling in a stream of argon, and they were reacted at the above temperature for 5 minutes. The reaction mixture was poured into ice water and alkalified by adding 10% sodium hydroxide. The aqueous layer was washed with ethyl acetate. The aqueous layer was acidified to a pH of about 5 with 10% hydrochloric acid, and extracted with methylene chloride. The methylene chloride layer was washed with water and a saturated aqueous solution of sodium chloride, and dried over anhydrous magnesium sulfate. The solvent was evaporated under reduced pressure to give 3,6-dimethyl-4-(3-nitrophenyl)-4,7-dihydroisothiazolo[5,4-b]pyridine-5-carboxylic acid in a yield of 64.9%.

In an argon stream, 24 ml of anhydrous tetrahydrofuran was added to a mixture of 260 mg (0.788 mM) of the resulting carboxylic acid, 1.19 g (7.88 mM) of S-(+)-2-methoxy-2-phenethyl alcohol and 179 mg (0.867 mM) of dicyclohexyl carbodiimide (DCC hereinafter) to form a solution. The solution was stirred at about 50° C. for 10 hours, and the temperature was returned to room temperature, and the mixture was stirred overnight. Then, 50 mg of DCC was added, and the mixture was further stirred at room temperature for 2 hours. Tetrahydrofuran was evaporated under reduced pressure, and the residue was extracted with ethyl acetate. The ethyl acetate layer was washed successively with 5% hydrochloric acid, a saturated aqueous solution of sodium hydrogen carbonate, water, and a saturated aqueous soution of sodium chloride, and dried over anhydrous magnesium sulfate. The solvent was evaporated under reduced pressure to give a diastereomeric mixture of 2-((S)-methoxy-2-phenyl)ethyl 3,6-dimethyl-4-(3-nitrophenyl)-4,7-dihydroisothiazolo[5,4-b]pyridine-5-carboxylate at the 4-position. It was subjected to silica gel column chromatography, and the column was eluted with a 50:1 mixture of methylene chloride and ethyl acetate to give 64.5 mg [29.5%; (+) diastereomer] of pale yellow visouis product. When the column was further eluted with a 50:2 mixture of methylene chloride and ethyl acetate, 96.5 mg [44.7%; (−) diastereomer] of a pale yellow viscous product was obtained.

(+) diastereomer

IR spectrum (neat cm$^{-1}$): 3350, 1690, 1670

NMR spectrum (CDCl$_3$): $\delta$ppm 2.10, 2.42 (each, 3H, s, CH$_3$) 3.25 (3H, s, OCH$_3$) 4.08–4.53 (3H, m, CH$_2$, CH) 5.22 (1H, s, CH) 6.68 (1H, bs, NH) 7.18–8.11 (4H, m, benzene ring H) 7.35 (5H, s, benzene ring H) $[\alpha]_D^{24}$+64.5° (c=0.637, CHCl$_3$)

(−) diastereomer

IR spectrum (neat cm$^{-1}$): 3450, 1690, 1670

NMR spectrum (CDCl$_3$): $\delta$ppm 2.10, 2.42 (each, 3H, s, CH$_3$) 3.29 (3H, s, OCH$_3$) 4.05–4.45 (3H, m, CH$_2$, CH) 5.21 (1H, s, CH) 6.68 (1H, bs, NH) 7.18–8.14 (4H, m, benzene ring H) 7.35 (5H, s, benzene ring H) $[\alpha]_D^{24}$−27.1° (c=0.965, CHCl$_3$)

EXAMPLE 54

Production of (+)-ethyl 3-[(R)-N-methyl-alpha-methylphenylethylaminomethyl]-6-methyl-4-(3-nitrophenyl)-4,7-dihydroisothiazolo[5,4-b]pyridne-5-carboxylate and (−)-ethyl 3-[(R)-N-methyl-alpha-methylphenylethylaminomethyl]-6-methyl-4-(3-nitrophenyl)-4,7-dihydroisothiazolo[5,4-b]pyridine-5-carboxylate To 604 mg (1.33 mM) of 3-methanesulfonyloxymethyl-6-methyl-4-(3-nitrophenyl)-4,7-dihydroisothiazolo[5,4-b]pyridine-5-carboxylate obtained in Example 3 was added 900 mg (6.67 mM) of R-(+)-N-methyl-alpha-methylbenzylamine, and in an argon stream, the mixture was stirred at about 65° to 85° C. for about 1 hour. After cooling, the reaction mixture was extracted with ethyl acetate containing 10% of hydrochloric acid. The ethyl acetate layer was washed successively with water, a saturated aqueous solution of sodium hydrogen carbonate, water and a saturated aqueous solution of sodium chloride, and dried over anhydrous sodium sulfate. The solvent was evaporated under reduced pressure to give a diastereomeric mixture of ethyl 3-[(R)-N-methyl-alpha-methylphenylethylaminomethyl]-6-methyl-4(3-nitrophenyl)-4,7-dihydroisothiazolo[5,4-b]pyridine-5-carboxylate at the 4-position. The mixture was subjected to silica gel column chromatography. The column was eluted with a 1:2 mixture of ethyl acetate and hexane to give 172 mg of yellow needles having a melting point of 137° to 138° C. [26.3% (+) diastereomer] and 76.5 mg of a pale yellow viscous product [15.5%, (−) diastereomer].

(+) diastereomer

IR spectrum (KBr, cm$^{-1}$): 3450, 1690

NMR spectrum (CDCl$_3$): $\delta$ppm 1.28 (3H, t, J=7.0 Hz, CH$_3$) 1.40 (3H, d, J=7.0 Hz, CH$_3$) 2.00 (3H, s, CH$_3$) 2.41 (3H, s, CH$_3$) 3.26 (2H, bs, CH$_2$) 3.65 (1H, q, J=7.0 Hz, CH) 4.14 (2H, q, J=7.0 Hz, CH) 5.59 (1H, s, CH) 7.08–8.11 (5H, m, benzene ring H) 7.27 (5H, s, benzene ring H) $[\alpha]_D^{24}$+217.0° (c=0.318, CHCl$_3$)

(−) diastereomer

IR spectrum (neat, cm$^{-1}$): 3300, 1690, 1670

NMR spectrum (CDCl$_3$): $\delta$ppm 1.29 (6H, d, t, J=7.0 Hz, CH$_3$×2) 1.98 (3H, s, CH$_3$) 2.40 (3H, s, CH$_3$) 3.30 (2H, bs, CH$_2$) 3.68 (1H, q, J=7.0 Hz, CH) 4.13 (2H, q, J=7.0 Hz, CH$_2$) 5.61 (1H, s, CH) 7.04–8.43 (5H, m, benzene ring H) 7.22 (5H, s, benzene ring H) $[\alpha]_D^{24}$+212.7° (c=0.765, CHCl$_3$)

In a similar manner, (+)-ethyl 3-[(S)-N-methyl-alpha-methylphenylethylaminomethyl]-6-methyl-4-(3-nitrophenyl)-4,7-dihydroisothiazolo[5,4-b]pyridine-5-carboxylate and (−)-ethyl 3-[(S)-N-methyl-alpha-methylphenylethylaminomethyl]-6-methyl-4-(3-nitrophenyl)-4,7-dihydroisothiazolo[5,4-b]pyridine-5-carboxylate were obtained from S-(−)-N-methyl-alpha-methylbenzylamine.

(+) diastereomer

Pale yellow viscous product Yield: 37.9% $[\alpha]_D^{24}$: +192.4° (c=1.63; CHCl$_3$).

The IR and NMR spectral data of this compound agreed with those of (−)-(R) diastereomer.

(−) diastereomer

Yellow needles Yield: 26.5% Melting point: 137° to 139° C. $[\alpha]_D^{24}$: −219.8° (c=0.30; CHCl$_3$)

The IR and NMR spectral data of this compound agreed with hose of the (+)-(R) diastereomer.

EXAMPLE 55

Production of (+)-ethyl 3-[2-((S)-alpha-methoxybenzylcarbonyloxy)ethyl]-6-methyl-4-(3-nitrophenyl)-4,7-dihydroisothiazolo[5,4-b]pyridine-5-carboxylate and (−)-ethyl 3-[2-((S)-alpha-methoxybenzylcarbonyloxy)ethyl]-6-methyl-4-(3-nitrophenyl)-4,7-dihydroisothiazolo[5,4-b]pyridine-5-carboxylate A diastereomeric mixture of ethyl 3-[2-((S)-alpha-methoxybenzylcarbonyloxy)ethyl]-6-methyl-4-(3-nitrophenyl)-4,7-dihydroisothiazolo[5,4-b]pyridine-5-carboxylate at the 4-position was produced by esterification reaction between (±)-ethyl 3-(2-hydroxyethyl)-6-methyl-4-(3-nitrophenyl)-4,7-dihydroisothiazolo[5,4-b]pyridine-5-carboxylate and S-(+)-alpha-methoxyphenylacetic acid. 717 mg of this mixture was recrystalized twice from 5 ml of ethanol to give 173 mg (48.5%) of yellow prisms having a melting point of 157° to 159° C. $[\alpha]_D^{24}$: +207.2° C., (c=1.04, CHCl$_3$). (−)-(S) diastereomer.

The recrystallization mother liquor was evaporated under reduced pressure to give 520 mg of a pale yellow jelly-like product which had a low optical purity and was levorotatory. The jelly-like product was subjected to high-performance liquid chromatography [column $\mu$-bondasphere 5$\mu$Si 100 Å 19 mm $\phi$×15 cm; moving phase CH$_2$Cl$_2$:AcOET *95:7), flow rate 36 ml/min.; UV detector 334 nm]. A fraction which showed a retention time of 16 minutes was separated to give 175 mg (48.8%) of (−)-ethyl 3-[2-((S)-alpha-methoxybenzylcarbonyloxy)ethyl]-6-methyl-4-(3-nitrophenyl)-4,7-dihydroisothiazolo[5,4-b]pyridine-5-carboxylate. $[\alpha]_D^{24}$: −207.4° (c=1.04, CHCl$_3$)

(+) diastereomer

IR spectrum (KBr cm$^{-1}$): 1720, 1680

NMR spectrum (CDCl$_3$): $\delta$ppm 1.25 (3H, t, J=7.0 Hz, CH$_3$) 2.31–2.90 (2H, m, CH$_2$) 2.46 (3H, s, CH$_3$) 3.39 (3H, s, CH$_3$) 3.90–4.63 (4H, m, CH$_2$×2) 4.73 (1H, s, CH) 5.26 (1H, s, CH) 6.80 (1H, bs, NH) 6.93–8.15 (10H, m, benzene ring H)

(−) diastereomer

IR spectrum (neat, cm$^{-1}$): 1740, 1690

NMR spectrum (CDCl$_3$): δppm 1.26 (3H, t, J=7.0 Hz, CH$_3$) 2.31–2.93 (2H, m, CH$_2$) 2.46 (3H, s, CH$_3$) 3.39 (3H, s, CH$_3$) 3.90–4.60 (4H, m, CH$_2$×2) 4.75 (1H, s, CH) 5.30 (1H, s, CH) 6.72 (1H, bs, NH) 7.14–8.21 (10H, m, benzene ring H)

EXAMPLE 56

Production of (+)-ethyl 3-[2-(4-phenyl-1-piperazinyl)ethyl]-6-methyl-4-(3-nitrophenyl)-4,7-dihydroisohiazolo[5,4-b]pyridine-5-carboxylate In an argon stream, 5 ml of ethanol was added to 130 mg (0.234 mM) of (+)-ethyl 3-[2-((S)-alpha-methoxybenzylcarboxnyloxy)ethyl]-6-methyl-4-(3-nitrophenyl)-4,7-dihydroisothiazolo[5,4-b]pyridine-5-carboxylate obtained in Example 55 to form a solution. While the solution was cooled with ice-sodium chloride, 5 ml of a 7% aqueous solution of potassium hydroxide was added, and the mixture was stirred at this temperature for 5 minutes. The reaction mixture was extracted with ethyl acetate, and the ethyl acetate layer was washed successively with a saturated aqueous solution of sodium hydrogen carbonate, water and a saturated aqueous solution of sodium chloride, and dried over anhydrous magnesium sulfate. The solvent was evaporated under reduced pressure to give (+)-ethyl 3-(2-hydroxyethyl)-6-methyl-4-(3-nitrophenyl)-4,7-dihydroisothiazolo[5,4-b]pyridine-5-carboxylate quantitatively.

$[\alpha]_D^{24}$: +183.1° (c=1.07, CHCl$_3$)

In an argon stream, 86 mg (0.221 mM) of the resulting carboxylate was dissolved in 1 ml of anhydrous tetrahydrofuran, and under ice cooling, 0.08 ml of triethylamine was added. Then, a solution of 0.03 ml of methanesulfonyl chloride in 0.5 ml of anhydrous tetrahydrofuran was added dropwise, and the mixture was stirred at the above temperature for 10 minutes. The reaction mixture was poured into 10% HCl-ice, and extracted with methylene chloride. The methylene chloride layer was washed with water and a saturated aqueous soltuion of sodium chloride, and dried over anhydrous magnesium sulfate. The solvent was evaporated under reduced pressure to give crude (+)-ethyl 3-(2-methanesulfonyloxyethyl)-6-methyl-4-(3-nitrophenyl)-4,7-dihydroisothiazolo[5,4-b]pyridine-5-carboxylate as a pale yellow jelly-like product.

To the jelly-like product was added 185 mg (1.105 mM) of 1-phenylpiperazine, and in an argon stream, the mixture was stirred at about 110° C. for 10 minutes. After cooling, the reaction mixture was subjected to silica gel column chromatography, and the column was eluted with a 100:1 mixture of chloroform and methanol to give 96.5 mg (82.0%) of (+)-ethyl 3-[2-(4-phenyl-1-piperazinyl)ethyl]-6-methyl-4-(3-nitrophenyl)-4,7-dihydroisothiazolo[5,4-b]pyridine-5-carboxylate as a pale yellow jelly-like product. Recrystallization of the jelly-like product from ether/hexane gave pale yellow needles having a melting point of 148° to 149° C.

$[\alpha]_D^{24}$: +196.8° (c=0.90, CHCl$_3$).

The IR and NMR spectral data of the resulting compound agreed with those of the racemate obtained in Example 17.

EXAMPLE 57

Production of (−)-ethyl 3-[2-(4-phenyl-1-piperazinyl)ethyl]-6-methyl-4-(3-nitrophenyl)-4,7-dihydroisothiazolo[5,4-b]pyridine-5-carboxylate In an argon stream, 5 ml of ethanol was added to 175 mg (0.329 mM) of (−)-ethyl 3-[2-((S)-alpha-methoxybenzylcarbonyloxy)ethyl]-6-methyl-4-(3-nitrophenyl)-4,7-dihydroisothiazolo[5,4-b]pyridine-5-carboxylate obtained in Example 55 to form a solution. While the solution was cooled with ice-sodium chloride, 7 ml of a 7% aqueous solution of potassium hydroxide was added, and the mixture was stirred at the above temperature for 5 minutes. The reaction mixture was extracted with ethyl acetate. The ethyl acetate layer was washed successively with a saturated aqueous solution of sodium hydrogen carbonate, water and a saturated aqueous solution of sodium chloride, and then dried over anhydrous magnesium sulfate. The solvent was evaporated under reduced pressure to give (−)-ethyl 3-(2-hydroxyethyl)-6-methyl-4-(3-nitrophenyl)-4,7-dihydroisothiazolo[5,4-b]pyridine-5-carboxylate quantitatively.

$[\alpha]_D^{24}$: −188.0° (c=1.04, CHCl$_3$).

The resulting carboxylate was then worked up as in Example 56 to give (−)-ethyl 3-[2-(4-phenyl-1-piperazinyl)ethyl]-6-methyl-4-(3-nitrophenyl)-4,7-dihydroisothiazolo[5,4-b]pyridine-5-carboxylate.

Yield: 78.7% Melting point: 148° to 149° C. $[\alpha]_D^{24}$: −196.0° (c=0.50, CHCl$_3$).

Similarly, 5.88 g of a diastereomeric mixture of ethyl 3-[2-((R)-alpha-methoxybenzylcarbonyloxy)ethyl]-6-methyl-4-(3-nitrophenyl)-4,7-dihydroisothiazolo[5,4-b]pyridine-5-carboxylate at the 4-position obtained by reacting (R)-(−)-alpha-methoxyphenylacetic acid and (±)-ethyl 3-(2-hydroxyethyl)-6-methyl-4-(3-nitrophenyl)-4,7-dihydroisothiazolo[5,4-b]pyridine-5-carboxylate was obtained by adding ether-hexane to the mixture, and recrystallized twice from 45 ml of ethanol with stirring to give 1.30 g (46.9%) of yellow prisms having a melting point of 157° to 159° C. [(−)-(R) diastereomer].

$[\alpha]_D^{24}$: −207.4° (c=1.04, CHCl$_3$).

The product was then worked up as in Example 56 to give (−)-ethyl 3-[2-(4-phenyl-1-piperazinyl)ethyl]-6-methyl-4-(3-nitrophenyl)-4,7-dihydroisothiazolo[5,4-b]pyridine-5-carboxylate.

Melting point: 148° to 149° C. $[\alpha]_D^{24}$: −196.0° (c=0.50, CHCl$_3$)

The IR and NMR spectral data of this product agreed with those of the racemate obtained in Example 17.

Some formulation examples of the compounds used in the Test Example given hereinabove are given below.

EXAMPLE 58

| Compound No. 70 (compound Ih) | 0.5 g |
|---|---|
| Potato starch | 1.5 g |
| Light Silicic anhydride | 0.5 g |
| Magnesium stearate | 0.1 g |
| Lactose | 7.4 g |

The above ingredients were mixed uniformly, and filled in hard capsules each in an amount of 200 mg.

EXAMPLE 59

| Compound No. 70 (compound Ih) | 2.5 g |
|---|---|
| Potato starch | 5.0 g |
| Crystalline cellulose | 3.0 g |
| Light silicic anhydride | 2.5 g |
| Hydroxypropyl cellulose | 1.5 g |
| Magnesium stearate | 0.75 g |
| Lactose | 34.75 g |

The active compound, lactose, potato starch, crystalline cellulose, and light silicic anhydride were mixed, and a 10% methanol solution of hydroxypropyl cellulose was added. The mixture was kneaded and granulated and extruded from a screen having an opening diameter of 0.8 mm. The granules were dried and then magnesium stearate was added. The granules were compression-molded into tablets each weighing 200 mg.

EXAMPLE 60

| Compound No. 21 (compound Ie) | 0.5 g |
|---|---|
| Polyethylene glycol 400 | 9.5 g |

The active compound was dissolved in polyethylene glycol 400, and the solution was filled in soft capsules each in an amount of 0.2 g.

EXAMPLE 61

| Compound No. 21 (compound Ie) | 0.05 g |
|---|---|
| Propylene glycol | 10.0 ml |

The active compound was dissolved in propylene glycol, aseptically filtered, and filled in ampoules each in an amount of 0.2 ml.

EXAMPLE 62

| Compound No. 13 (compound Id) | 0.25 g |
|---|---|
| Polyethylene glycol 1500 | 30.0 g |
| Polyethylene glycol 6000 | 19.75 g |

The above ingredients were heat-melted and uniformly mixed, and then cast into plastic molds. After cooling, suppositories each weighting 1 g were obtained.

What is claimed is:

1. A 4,7-dihydroisothiazolo[5,4-b]pyridine derivative represented by the general formula

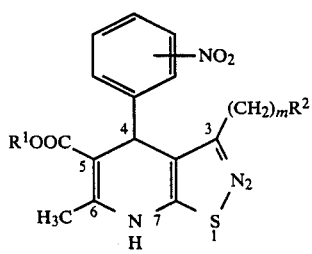

I wherein
$R^1$ represents an alkyl group which may be substituted,
$R^2$ represents a hydroxyl group, a benzyloxy group, a lower alkoxy group, a group of the formula

in which $R^3$ and $R^4$ are identical or different and each represents a hydrogen atom, a lower alkyl group, an aralkyl group, an aralkynyl group, an aryloxyalkyl group, an arylaminoalkyl group, a pyridylalkyl group or a benzazolylalkyl group, or $R^3$ and $R^4$ form a ring and represent a group of the formula

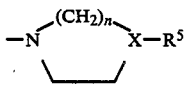

where X represents a methine group, a a nitrogen atom or an oxygen atom, n is an integer of 1 or 2, and when X is a methine group or a nitrogen atom, $R^5$ represents a hydrogen atom, a lower alkyl group, a lower hydroxyalkyl group, an aryl group, an aryloxy group, an aralkyl group, a furoyl group, a pyridyl group or a diphenylmethane group each of which may be substituted, and m is an integer of 1 to 3; or an acid addition salt thereof.

2. The compound of claim 1 which is an optically active compound.

3. A 4,7-dihydroisothiazolo[5,4-b]pyridine derivative represented by the general formula

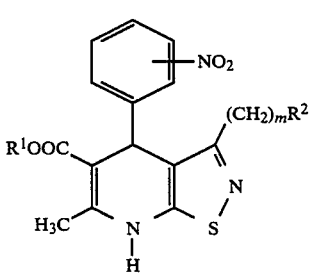

(I)

wherein
$R^1$ represents an alkyl group which may be substituted,
$R^2$ represents a hydroxyl group, a benzyloxy group, a lower alkoxy group, or a group of the formula

in which $R^3$ and $R^4$ are identical or different and each represents a hydrogen atom, a lower alkyl group, an aryloxyalkyl group or a pyridylalkyl group, and m is an integer of 1 to 3; or an acid addition salt thereof.

4. An agent for treating cardiovascular diseases, said agent comprising as an active ingredient a 4,7-dihydroisothiazolo[5,4-b]pyridine derivative represented by the general formula

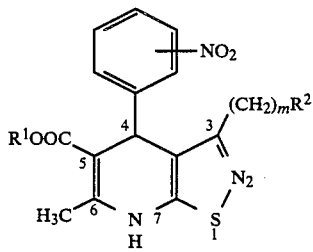

I wherein

R¹ represents an alkyl group which may be substituted,

R² represents a hydroxyl group, a benzyloxy group, a lower alkoxy group, a group of the formula

in which $R^3$ and $R^4$ are identical or different and each represents a hydrogen atom, a lower alkyl group, an aralkyl group, an aralkynyl group, an aryloxyalkyl group, an arylaminoalkyl group, a pyridylalkyl group or a benzoazolylalkyl group, or $R^3$ and $R^4$ form a ring and represent a group of the formula

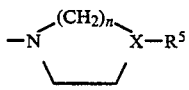

where X represents a methine group, a nitrogen atom or an oxygen atom, n is an integer of 1 or 2, and when X is a methine group or a nitrogen atom, $R^5$ represents a hydrogen atom, a lower alkyl group, a lower hydroxyalkyl group, an aryl group, an aryloxy group, an aralkyl group, a furoyl group, a pyridyl group or a diphenylmethane group each of which may be substituted, and m is an integer of 1 to 3; or an acid addition salt thereof and a pharmaceutically accepted carrier.

* * * * *